US011747329B2

(12) United States Patent
Bedau

(10) Patent No.: US 11,747,329 B2
(45) Date of Patent: Sep. 5, 2023

(54) MAGNETIC GRADIENT CONCENTRATOR/RELUCTANCE DETECTOR FOR MOLECULE DETECTION

(71) Applicant: Western Digital Technologies, Inc., San Jose, CA (US)

(72) Inventor: Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 662 days.

(21) Appl. No.: 16/823,592

(22) Filed: Mar. 19, 2020

(65) Prior Publication Data

US 2021/0156851 A1 May 27, 2021

Related U.S. Application Data

(60) Provisional application No. 62/938,984, filed on Nov. 22, 2019.

(51) Int. Cl.
*G01N 33/543* (2006.01)
*G01N 33/58* (2006.01)
(Continued)

(52) U.S. Cl.
CPC ........ *G01N 33/54326* (2013.01); *B01L 3/502* (2013.01); *C12Q 1/6869* (2013.01);
(Continued)

(58) Field of Classification Search
CPC ........... G01N 33/54326; G01N 27/745; G01N 33/542; G01N 33/54373; G01N 33/573;
(Continued)

(56) References Cited

U.S. PATENT DOCUMENTS 5,200,084 A * 4/1993 Liberti .................... B03C 1/002
436/526
5,302,509 A 4/1994 Cheeseman
(Continued)

FOREIGN PATENT DOCUMENTS

CN 102928596 A 2/2013
CN 103885000 A 6/2014
(Continued)

OTHER PUBLICATIONS

Machine Translation of EP 2674264. Retrieved Sep. 14, 2022 (Year: 2022).*
(Continued)

*Primary Examiner* — Matthew D Krcha
*Assistant Examiner* — Tingchen Shi

(57) ABSTRACT

Disclosed herein are devices for molecule detection and methods for using detection devices for molecule detection, such as nucleic acid sequencing. In some embodiments, a detection device comprises one or more pole pieces, one or more sensors, each of the one or more sensors coupled to at least one of the one or more pole pieces, and detection circuitry coupled to the one or more sensors. The detection circuitry is configured to detect a characteristic of each of the one or more sensors, the characteristic indicating presence or absence of one or more magnetic nanoparticles (MNPs) coupled to at least one of a plurality of molecules to be detected, and at least one of the one or more pole pieces is operable to draw the one or more MNPs toward at least one of the one or more sensors.

30 Claims, 12 Drawing Sheets

(51) Int. Cl.
*G01N 33/573* (2006.01)
*G01N 33/542* (2006.01)
*C12Q 1/6869* (2018.01)
*B01L 3/00* (2006.01)
*G01N 27/74* (2006.01)

(52) U.S. Cl.
CPC ......... *G01N 27/745* (2013.01); *G01N 33/542* (2013.01); *G01N 33/54373* (2013.01); *G01N 33/573* (2013.01); *G01N 33/585* (2013.01)

(58) Field of Classification Search
CPC ............ G01N 33/585; G01N 33/54346; B01L 3/502; C12Q 1/6869
See application file for complete search history.

(56) References Cited

U.S. PATENT DOCUMENTS

| | | | |
|---|---|---|---|
| 6,037,167 | A | 3/2000 | Adelman et al. |
| 6,046,585 | A * | 4/2000 | Simmonds ........... G01N 27/745 |
| | | | 436/526 |
| 6,197,520 | B1 | 3/2001 | Wittwer et al. |
| 6,406,848 | B1 | 6/2002 | Bridgham et al. |
| 6,654,505 | B2 | 11/2003 | Bridgham et al. |
| 6,806,052 | B2 | 10/2004 | Bridgham et al. |
| 6,831,994 | B2 | 12/2004 | Bridgham et al. |
| 6,833,246 | B2 | 12/2004 | Balasubramanian |
| 6,905,736 | B1 | 6/2005 | Chow et al. |
| 6,969,488 | B2 | 11/2005 | Bridgham et al. |
| 6,969,679 | B2 | 11/2005 | Okamura et al. |
| 7,057,026 | B2 | 6/2006 | Barnes et al. |
| 7,115,400 | B1 | 10/2006 | Adessi et al. |
| 7,282,370 | B2 | 10/2007 | Bridgham et al. |
| 7,382,586 | B2 | 6/2008 | Carey et al. |
| 7,405,281 | B2 | 7/2008 | Xu et al. |
| 7,414,116 | B2 | 8/2008 | Milton et al. |
| 7,427,673 | B2 | 9/2008 | Balasubramanian et al. |
| 7,473,031 | B2 | 1/2009 | Wolkin et al. |
| 7,541,444 | B2 | 6/2009 | Milton et al. |
| 7,566,537 | B2 | 7/2009 | Balasubramanian et al. |
| 7,771,973 | B2 | 8/2010 | Milton et al. |
| 7,772,384 | B2 | 8/2010 | Balasubramanian et al. |
| 7,920,032 | B2 | 4/2011 | Makinwa et al. |
| 8,053,244 | B2 | 11/2011 | Ryan et al. |
| 8,058,031 | B2 | 11/2011 | Xu et al. |
| 8,071,739 | B2 | 12/2011 | Milton et al. |
| 8,130,072 | B2 | 3/2012 | De Bruyker et al. |
| 8,158,346 | B2 | 4/2012 | Balasubramanian et al. |
| 8,252,910 | B2 | 8/2012 | Korlach et al. |
| 8,259,409 | B2 | 9/2012 | Braganca et al. |
| 8,361,713 | B2 | 1/2013 | Bridgham et al. |
| 8,367,813 | B2 | 2/2013 | Korlach |
| 8,432,644 | B2 | 4/2013 | Braganca et al. |
| 8,462,461 | B2 | 6/2013 | Braganca et al. |
| 8,513,029 | B2 | 8/2013 | Zhou |
| 8,553,346 | B2 | 10/2013 | Braganca et al. |
| 8,570,677 | B2 | 10/2013 | Braganca et al. |
| 8,597,881 | B2 | 12/2013 | Milton et al. |
| 8,652,810 | B2 | 2/2014 | Adessi et al. |
| 8,654,465 | B2 | 2/2014 | Braganca et al. |
| 8,675,309 | B2 | 3/2014 | Braganca et al. |
| 8,728,729 | B2 | 5/2014 | Bridgham et al. |
| 8,728,825 | B2 | 5/2014 | Wang et al. |
| 9,121,062 | B2 | 9/2015 | Balasubramanian et al. |
| 9,273,354 | B2 | 3/2016 | Bridgham et al. |
| 9,297,006 | B2 | 3/2016 | Adessi et al. |
| 9,435,791 | B2 | 9/2016 | Acosta et al. |
| 9,453,258 | B2 | 9/2016 | Kain et al. |
| 9,464,107 | B2 | 10/2016 | Wegener et al. |
| 9,587,275 | B2 | 3/2017 | Emig et al. |
| 9,605,310 | B2 | 3/2017 | Balasubramanian et al. |
| 9,640,748 | B2 | 5/2017 | Gotsmann et al. |
| 10,203,379 | B2 | 2/2019 | Wang et al. |
| 10,260,095 | B2 | 4/2019 | Esfandyarpour et al. |
| 10,591,440 | B2 | 3/2020 | Astier et al. |
| 11,112,468 | B2 | 9/2021 | Braganca |
| 2004/0043479 | A1 | 3/2004 | Briscoe et al. |
| 2004/0219695 | A1 | 11/2004 | Fox |
| 2005/0054081 | A1 | 3/2005 | Hassard et al. |
| 2005/0118102 | A1 | 6/2005 | Xiang et al. |
| 2007/0224700 | A1 * | 9/2007 | Masters ........... B01L 3/502761 |
| | | | 422/68.1 |
| 2007/0264159 | A1 | 11/2007 | Graham et al. |
| 2008/0218165 | A1 | 9/2008 | Kahlman et al. |
| 2008/0241569 | A1 | 10/2008 | Qin et al. |
| 2009/0148857 | A1 | 6/2009 | Srivastava et al. |
| 2009/0206832 | A1 | 8/2009 | Kahlman et al. |
| 2009/0208957 | A1 | 8/2009 | Korlach et al. |
| 2010/0039105 | A1 | 2/2010 | Ryan et al. |
| 2010/0111768 | A1 | 5/2010 | Banerjee et al. |
| 2010/0194386 | A1 | 8/2010 | Prins et al. |
| 2010/0207631 | A1 | 8/2010 | McDowell |
| 2010/0231214 | A1 | 9/2010 | Zhou |
| 2011/0223612 | A1 | 9/2011 | Wang et al. |
| 2012/0295262 | A1 | 11/2012 | Ronaghi et al. |
| 2014/0008281 | A1 | 1/2014 | Ramanathan et al. |
| 2014/0139214 | A1 | 5/2014 | Park et al. |
| 2014/0292318 | A1 | 10/2014 | Wang et al. |
| 2016/0131613 | A1 * | 5/2016 | Jayant ................ G01N 27/4145 |
| | | | 257/253 |
| 2017/0304825 | A1 | 10/2017 | Issadore et al. |
| 2018/0074016 | A1 | 3/2018 | Chen et al. |
| 2018/0100190 | A1 | 4/2018 | Esfandyarpour et al. |
| 2018/0128822 | A1 | 5/2018 | Wang et al. |
| 2018/0237850 | A1 * | 8/2018 | Mandell .............. C12Q 1/6869 |
| 2018/0284200 | A1 | 10/2018 | Chen et al. |
| 2019/0032114 | A1 | 1/2019 | Trivedi |
| 2019/0170680 | A1 | 6/2019 | Sikora et al. |
| 2019/0390267 | A1 | 12/2019 | Astier et al. |
| 2020/0324283 | A1 | 10/2020 | Braganca et al. |
| 2020/0326309 | A1 | 10/2020 | Braganca et al. |
| 2020/0326335 | A1 | 10/2020 | Braganca et al. |
| 2020/0326392 | A1 | 10/2020 | Braganca et al. |
| 2021/0047681 | A1 | 2/2021 | Mendonsa et al. |
| 2021/0047682 | A1 | 2/2021 | Mendonsa et al. |
| 2021/0079455 | A1 | 3/2021 | Braganca et al. |

FOREIGN PATENT DOCUMENTS

| | | | |
|---|---|---|---|
| CN | 107873060 A | 4/2018 | |
| CN | 108138229 A | 6/2018 | |
| CN | 107051597 B | 8/2019 | |
| EP | 1544310 A2 | 6/2005 | |
| EP | 2674264 A2 * | 12/2013 | .............. B25J 15/04 |
| EP | 3208627 A1 | 8/2017 | |
| WO | 2005047864 A3 | 9/2005 | |
| WO | WO-2005124345 A2 * | 12/2005 | .............. B03C 1/01 |
| WO | 2015031691 A1 | 3/2015 | |
| WO | 2016183218 A1 | 11/2016 | |
| WO | 2017030999 A1 | 2/2017 | |
| WO | 2017061129 A1 | 4/2017 | |
| WO | 2018017884 A1 | 1/2018 | |
| WO | 2018186539 A1 | 10/2018 | |
| WO | 2019068204 A1 | 4/2019 | |
| WO | 2020210370 A1 | 10/2020 | |

OTHER PUBLICATIONS

Daschiel et al. The holy grail of microfluidics: sub-laminar drag by layout of periodically embedded microgrooves (2013) MicrofluidNanofluid 15, 675-687.

Mao et al. A Microfluidic Device with a Linear Temperature Gradient for Parallel and Combinatorial Measurements (2002) J AmChem Soc 124, 4432-4435.

Qiu et al. Instrument-free point-of-care molecular diagnosis of H 1 N 1 based on microfluidic convective PCR (2017) Sensors andActuators B: Chemical 243, 738-744.

E. du Trémolet de Lacheisserie, D. Gignoux, and M. Schlenker (editors), Magnetism: Materials and Applications, vol. 2. Springer, 2005.

E. Hall, "On a New Action of the Magnet on Electric Currents," American Journal of Mathematics, vol. 2, 287, 1879.

(56) References Cited

OTHER PUBLICATIONS

G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.

International Search Report and Written Opinion from PCT Application No. PCT/US2020/027290 (filed Apr. 8, 2020), dated Jun. 25, 2020.

International Search Report and Written Opinion from PCT Application No. PCT/US2019/068131 (filed Dec. 20, 2019), dated Apr. 1, 2020.

International Search Report and Written Opinion from PCT Application No. PCT/US2019/068535 (filed Dec. 26, 2019), dated Apr. 26, 2020.

International Search Report and Written Opinion from PCT Application No. PCT/US2020/014707 (filed Jan. 23, 2020), dated May 11, 2020.

International Search Report and Written Opinion from PCT Application No. PCT/US2020/021776 (filed Mar. 9, 2020), dated Sep. 1, 2020.

International Search Report and Written Opinion from PCT Application No. PCT/US2020/023069 (filed Mar. 17, 2020), dated Jul. 20, 2020.

International Search Report and Written Opinion from PCT Application No. PCT/US2020/023078 (filed Mar. 17, 2020), dated Jul. 19, 2020.

International Search Report and Written Opinion from PCT Application No. PCT/US2020/035915 (filed Jun. 3, 2020), dated Aug. 26, 2020.

J. C. Slonczewski, "Current-driven excitation of magnetic multilayers," Journal of Magnetism and Magnetic Materials, vol. 159, L1, 1996.

L. Berger, "Emission of spin waves by a magnetic multilayer traversed by a current," Physical Review B, vol. 54, 9353, 1996.

Lany, M., G. Boero, and R. S. Popovic. "Superparamagnetic microbead inductive detector". Review of scientific instruments 76.8 (2005): 084301.

Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.

M. Díaz-Michelena, "Small Magnetic Sensors for Space Applications," Sensors, vol. 9, 2271, 2009.

Michael L. Metzker, "Sequencing Technologies—the Next Generation," Nature Rev. Genet. 11: 31-46 (2009).

Miller, M. M., et al. "A DNA array sensor utilizing magnetic microbeads and magnetoelectronic detection". Journal of Magnetism and Magnetic Materials 225.1-2 (2001): 138-144.

P. Anderson, J. Rowell, "Probable Observation of the Josephson Superconducting Tunneling Effect," Physical Review Letters, vol. 10, 230, 1963.

P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.

P. Namdari, H. Daraee, and A. Eatemadi, "Recent Advances in Silicon Nanowire Biosensors: Synthesis Methods, Properties and Applications", Nanoscale Research Letters, vol. 11, 406, 2016.

Quynh, L. K., et al. Detection of magnetic nanoparticles using simple AMR sensors in Wheatstone bridge. Journal of Science: Advanced Materials and Devices, 2016, 1.1: 98-102.

R. C. Jaklevic, J. Lambe, A. H. Silver & J. E. Mercereau, "Quantum Interference Effects in Josephson Tunneling," Physical Review Letters, vol. 12, 159, 1964.

R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions On Magnetics, vol. 48, 1758, 2012.

Rabehi, A., Electromagnetic microsystem for the detection of magnetic nanoparticles in a microfluidic structure for immunoassays (Doctoral dissertation). Jan. 29, 2020.

Rauwerdink, A. M., Giustini, A. J., & Weaver, J. B. (2010). Simultaneous quantification of multiple magnetic nanoparticles. Nanotechnology, 21(45), 455101.

Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.

Srimani T. et al., "High Sensitivity Biosensor using Injection Locked Spin Torque Nano-Oscillators," arXiv: 1511.09072, Nov. 2015.

Tang, C., He, Z., Liu, H., Xu, Y., Huang, H., Yang, G., . . . & Chen, Z. (2020). Application of magnetic nanoparticles in nucleic acid detection. Journal of Nanobiotechnology, 18, 1-19. Apr. 21, 2020.

Wang, W., & Jiang, Z., "Thermally assisted magnetic tunneling junction for biosensing applications," IEEE Transactions on Magnetics, 43(6), 2406-2408, Jun. 30, 2007.

Weijun Zhou, et al., "Novel dual fluorescence temperature-sensitive chameleon DNA-templated nanocluster pair for intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).

Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.

Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.

Ye, F., Zhao, Y., El-Sayed, R., Muhammed, M., & Hassan, M. (2018). Advances in nanotechnology for cancer biomarkers. Nano Today, 18, 103-123.

Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.

International Search Report and Written Opinion from PCT Application No. PCT/US2021/021274 (filed Mar. 7, 2021), dated Sep. 28, 2021.

International Search Report and Written Opinion from PCT Application No. PCT/US2021/028263 (filed Apr. 21, 2021), dated Aug. 26, 2021.

International Search Report and Written Opinion from PCT Application No. PCT/US2021/040767 (filed Jul. 8, 2021), dated Oct. 25, 2021.

A. Seki, et al., "Study of the heating characteristics and mechanisms of magnetic nanoparticles over a wide range of frequencies and amplitudes of an alternating magnetic field," Journal of Physics: Conference Series 521 (2014).

A.M. Sydor et al., "Super-Resolution Microscopy: From Single Molecules to Supramolecular Assemblies," Trends in Cell Biology, Dec. 2015, vol. 25, No. 12, pp. 730-748.

B. N. Engel, et al., "A4-Mb Toggle MRAM Based on a Novel Bit and Switching Method," IEEE Transactions on Magnetics, vol. 41, No. 1, Jan. 2005.

C. Chappert et al., "The emergence of spin electronics in data storage," Nature Materials, Dec. 2007.

C.H. Smith et al., "High-resolution giant magnetoresistance on-chip arrays for magnetic imaging," Journal of Applied Physics 93, 6864 (2003).

D. Ross et al., "Temperature Measurement in Microfluidic Systems Using a Temperature-Dependent Fluorescent Dye," Anal. Chem. 2001, 73, 17, 4117-4123, Jul. 24, 2001.

EPHOTOzine.com, "Complete Guide To Image Sensor Pixel Size," Aug. 2, 2016, available at https://www.ephotozine.com/article/complete-guide-to-image-sensor-pixel-size-29652.

F. Grasset et al., "Synthesis, magnetic properties, surface modification and cytotoxicity evaluation of $Y_3Fe_{5-x}Al_xO_{12}$ (0?x?2) garnet submicron particles for biomedical applications," Journal of Magnetism and Magnetic Materials, vol. 234, Issue 3, Sep. 2001, pp. 409-418.

(56) References Cited

OTHER PUBLICATIONS

F. Menges et al., "Temperature mapping of operating nanoscale devices by scanning probe thermometry," Nature Communications, 7:10874, Mar. 3, 2016.

Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).

Illumina, "NovaSeq 6000 Sequencing System," 2019, available at https://www.illumina.com/systems/sequencing-platforms/novaseq.html.

International Search Report from PCT App. No. PCT/US2016/046888, dated Oct. 26, 2016.

J. Sakakibara et al., "Measurements of thermally stratified pipe flow using image-processing techniques," Experiments in Fluids, Dec. 1993, vol. 16, Issue 2, pp. 82-96.

John Pearce, et al., "Magnetic Heating of Nanoparticles: The Importance of Particle Clustering to Achieve Therapeutic Temperatures," Journal of Nanotechnology in Engineering and Medicine, Feb. 2014, vol. 4 /011007-1.

Lin Gui and Carolyn L. Ren, "Temperature measurement in microfluidic chips using photobleaching of a fluorescent thin film," Applied Physics Letters 92, 024102, 2008.

M. Aslam et al., "Silica encapsulation and magnetic properties of FePt nanoparticles," Journal of Colloid and Interface Science 290 (2005) 444-449.

M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.

M.T. Tlili et al., "Magnetic, Electrical Properties and Spin-Glass Effect of Substitution of Ca for Pr in Ca2-xPrxMnO4 Compounds," The Open Surface Science Journal, 2009, vol. 1, pp. 54-58.

N. X. Phuc, et al., "Tuning of the Curie Temperature in La1-xSrxMn1-yTiyO3" J. Korean Phy. Soc., vol. 52, No. 5, May 2008, pp. 1492-1495.

N.R. Patil et al., "Effect of temperature on the fluorescence emission of ENCTTTC in different nonpolar solvents," Can. J. Phys. 91: 971-975 (2013).

R. Giri, "Temperature effect study upon the fluorescence emission of substituted coumarins," Spectrochimica Acta Part A: Molecular Spectroscopy, vol. 48, Issue 6, Jun. 1992, p. 843-848.

S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.

S.I. Kiselev et al., "Microwave oscillations of a nanomagnet driven by a spin-polarized current," Nature 425, pp. 380-383, 2003.

T. Nagasawa et al., "Delay detection of frequency modulation signal from a spin-torque oscillator under a nanosecond-pulsed magnetic field," Journal of Applied Physics, vol. 111, 07C908 (2012).

W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.

Weifeng Shen et al., "Detection of DNA labeled with magnetic nanoparticles using MgO-based magnetic tunnel junction sensors," Journal of Applied Physics 103, 07A306 (2008).

Y. Astier, et al., U.S. Appl. No. 62/833,130, "Nucleic Acid Sequencing by Systhesis Using Magnetic Sensor Arrays," filed Apr. 12, 2019.

\* cited by examiner

MAGNETIC GRADIENT CONCENTRATOR/RELUCTANCE DETECTOR FOR MOLECULE DETECTION

CROSS-REFERENCE TO RELATED APPLICATIONS

This application claims the benefit of, and hereby incorporates by reference the entirety of the contents of, U.S. Provisional Application No. 62/938,984, filed Nov. 22, 2019 and entitled "Magnetic Gradient Concentrator/Reluctance Detector for Molecule Detection."

BACKGROUND

Sequencing by synthesis (SBS) is a type of nucleic acid sequencing used, for example, for DNA sequencing. SBS involves binding of primer-hybridized template DNA, incorporation of a deoxynucleoside triphosphate (dNTP), and detection of incorporated dNTP. Conventional SBS for DNA sequencing relies on the detection of fluorescence. Specifically, fluorescence-based technologies used to differentiate between different bases in a sample (e.g., in fluorescence-based nucleic acid sequencing technologies) rely on, for example, the quality of a signal generated by a detection moiety that is associated with a particular type of nucleotide. For example, conventional fluorescent sequencing technologies utilize identifiably-distinct fluorescent moieties, each attached to one of the four nucleotides A, T, C, and G that are utilized in a sequencing reaction.

One conventional method of DNA sequencing involves adapting single-strand DNA (ssDNA) for attachment to a solid support of a sequencing apparatus and amplifying the quantity of the ssDNA using techniques such as the polymerase chain reaction (PCR) to create many DNA molecules with a short leader. The PCR is a process in which a single DNA molecule can be amplified (replicated) by orders of magnitude into thousands or even millions of copies of the molecule. The process relies on cycling a PCR mixture containing polymerase, dNTPs, sample DNA template, and primers through different temperatures. At a first, high-temperature range, denaturation occurs as the paired strands of the double-stranded sample DNA template separate into two individual strands. At a second, low-temperature range, annealing of primers complementary to the region of the sample DNA template being targeted for amplification takes place. At a third, mid-temperature range, extension of the complementary sequence from the primer occurs, during which the polymerase adheres to the primer and uses nucleotides to replicate each isolated sample DNA template strand. This cycle is typically repeated multiple (typically many) times to increase the amount of replicated DNA on an exponential basis until the desired amount is present for a particular experiment.

Following amplification, an oligo complementary to the short leader may be added so that there is a short section of double-stranded DNA (dsDNA) at the leader. The double stranded portion of the bound molecule is a primer for a suitable DNA polymerase, such as, for example, Taq polymerase, which is operable at high temperatures.

The sequencing procedure can then take one of several approaches. For example, the sequencing can use a mixture of four fluorescently-labeled 3'-blocked NTPs (fluorescently labeled dideoxynucleotide terminators), where the fluorescent label is part of the 3'-blocking group. The fluorescent label serves as a "reversible terminator" for polymerization. Each of the NTPs is labeled by a different label (i.e., each of the A, G, C, and T nucleotides has a different label), and the different labels are distinguishable by fluorescent spectroscopy or by other optical means.

In conventional sequencing approaches, four fluorescently-labeled nucleotide precursors are used to sequence millions of clusters of DNA strands in parallel. DNA polymerase catalyzes the incorporation of fluorescently-labeled dNTPs into a DNA template strand during sequential cycles of DNA synthesis. In each sequencing cycle, the bound double strand DNA molecule is exposed to DNA polymerase and a mixture of the four fluorescently-labeled 3'-blocked NTPs. The polymerase adds one of the four dNTPs to the growing oligonucleotide chain (whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA.

Because only one of the four types of dNTP will have been added to the oligonucleotide, and the four fluorescent labels are distinguishable, the identity of the incorporated dNTP can be identified through laser excitation and imaging. Specifically, each of four filters is used to determine whether light of a particular wavelength (e.g., color) is emitted. The fluorescent label can then be enzymatically cleaved to allow the next round of incorporation. Because each base type can pair with one and only one other base type, the identity of the just-paired base in the unknown sequence of the ssDNA is known from the identity of the incorporated dNTP (which is known from the wavelength of emitted light). Thus, the base is identified directly from fluorescence measurements during each cycle.

One disadvantage of the above-described approach is that a complicated optics system is needed to filter out different wavelengths of light to detect the fluorescent labels of the incorporated dNTPs and to distinguish between the different emitted colors. Other approaches have been developed to simplify the optics system, but they are slower to sequence and require intermediate chemistry steps within each sequencing cycle. Thus, these approaches have been introduced in smaller, less expensive entry-level sequencing systems but not in higher-level systems requiring fast throughput.

Accordingly, there is a need to improve DNA sequencing and, generally, molecule detection.

SUMMARY

This summary represents non-limiting embodiments of the disclosure.

In some embodiments, a detection device comprises one or more pole pieces, one or more sensors, each of the one or more sensors coupled to at least one of the one or more pole pieces, and detection circuitry coupled to the one or more sensors. In some embodiments, the detection circuitry is configured to detect a characteristic of each of the one or more sensors, where the characteristic indicates presence or absence of one or more magnetic nanoparticles (MNPs) coupled to at least one of a plurality of molecules to be detected. The characteristic detected by the detection circuitry may comprise a voltage, current, resistance, frequency, phase, noise, or temperature; a change in voltage, current, resistance, frequency, phase, noise, or temperature; or a change in a statistical property (e.g., mean, variance, standard deviation, etc.) of voltage, current, resistance, frequency, phase, noise, or temperature. In some embodiments, at least one of the one or more pole pieces is operable to draw the one or more MNPs toward at least one of the one or more sensors. The one or more sensors may comprise one or more of a temperature sensor, a magnetoresistive (MR) sensor, a magnetic tunnel junction (MTJ), a spin-torque oscillator (STO), or a spin valve.

In some embodiments, the detection device also has at least one reagent area configured to hold fluid containing the plurality of molecules to be detected. The at least one reagent area may comprise a fluidic channel. In some embodiments having at least one reagent area, one or more surfaces within the reagent area provide one or more sites for binding the plurality of molecules to be detected, the one or more sites being located among the one or more sensors. At least one magnetic shield may be disposed between at least two of the one or more sites.

In some embodiments, the detection device also includes a barrier material (e.g., an insulator or a metal) encapsulating the one or more sensors and for providing a barrier between the one or more sensors and the at least one of the plurality of molecules to be detected.

In some embodiments, the one or more pole pieces comprises at least one line coupling at least one of the one or more sensors to the detection circuitry. In some embodiments, at least one of the one or more pole pieces has a conical, triangular, or pyramidal shape. In some embodiments, at least one of the one or more pole pieces is configured to assist in creating a magnetic field gradient for drawing at least a portion of the one or more MNPs toward one or more of the one or more sensors.

The detection device may further comprise one or more solenoids or ferromagnetic components. In some such embodiments, at least one of the one or more sensors is disposed between its respective one of the one or more pole pieces and a respective one of the one or more solenoids or ferromagnetic components.

In some embodiments comprising a one or more solenoids or ferromagnetic components, the detection device further comprises one or more yokes, wherein at least one of the one or more solenoids or ferromagnetic components is disposed between its respective sensor and a respective one of the one or more yokes, thereby forming one or more magnetic circuits. In some such embodiments, at least one ferromagnetic component has a coercivity enabling the ferromagnetic component to be selectively magnetized or selectively demagnetized by an external magnetic field. A remanence of each ferromagnetic component may be selected to enable the ferromagnetic component to detect the one or more MNPs.

In some embodiments, the detection device further comprises at least one magnetic component configured to generate a magnetic field through the one or more pole pieces.

In some embodiments, the one or more sensors comprise a plurality of sensors disposed in a cross-point array comprising a first top line, a second top line, a first bottom line, and a second bottom line, and the first top line is coupled to the first bottom line at a first location, the first top line is coupled to the second bottom line at a second location, the second top line is coupled to the first bottom line at a third location, and the second top line is coupled to the second bottom line at a fourth location. In some such embodiments, the first and second top lines are substantially parallel to each other, the first and second bottom lines are substantially parallel to each other, and the first and second top lines are substantially perpendicular to the first and second bottom lines.

In some embodiments, the detection device is a sequencing device, and the plurality of molecules to be detected comprises biologic molecules (e.g., nucleic acids).

In some embodiments, the detection circuitry comprises one or more selector devices, and at least one of the one or more selector devices is coupled to a respective one of the one or more sensors. In some embodiments in which the detection circuitry comprises one or more selector devices, at least one of the one or more selector devices comprises a transistor. In some embodiments in which the detection circuitry comprises one or more selector devices, at least one of the one or more selector devices comprises an in-stack selector.

In some embodiments, the one or more sensors comprise a plurality of sensors, wherein a first subset of the plurality of sensors is arranged in a first row, a second subset of the plurality of sensors is arranged in a second row that is substantially parallel to the first row, and at least one reagent area is disposed between the first and second rows.

In some embodiments, a method of using a detection device that comprises one or more pole pieces, one or more sensors, a reagent area, and detection circuitry comprises labeling a nucleotide precursor with one or more MNPs, adding the labeled nucleotide precursor to the reagent area, detecting a characteristic of at least one of the one or more sensors, and, for that sensor, based at least in part on the detected characteristic, determining whether the labeled nucleotide precursor has been detected. In some embodiments, the method further comprises binding a nucleic acid strand to be sequenced to the detection device in the reagent area before adding the labeled nucleotide precursor to the reagent area. In some embodiments, the method further comprises applying a magnetic field to the detection device and, using the detection circuitry, detecting the characteristic of at least one of the one or more sensors while the magnetic field is being applied. In some embodiments, after detecting the characteristic of the at least one of the one or more sensors, the magnetic field is turned off and, while the magnetic field is off, the MNPs are removed (e.g., cleaved) and the reagent area is washed.

BRIEF DESCRIPTION OF THE DRAWINGS

Objects, features, and advantages of the disclosure will be readily apparent from the following description of certain embodiments taken in conjunction with the accompanying drawings in which.

DETAILED DESCRIPTION

Figure 1A:
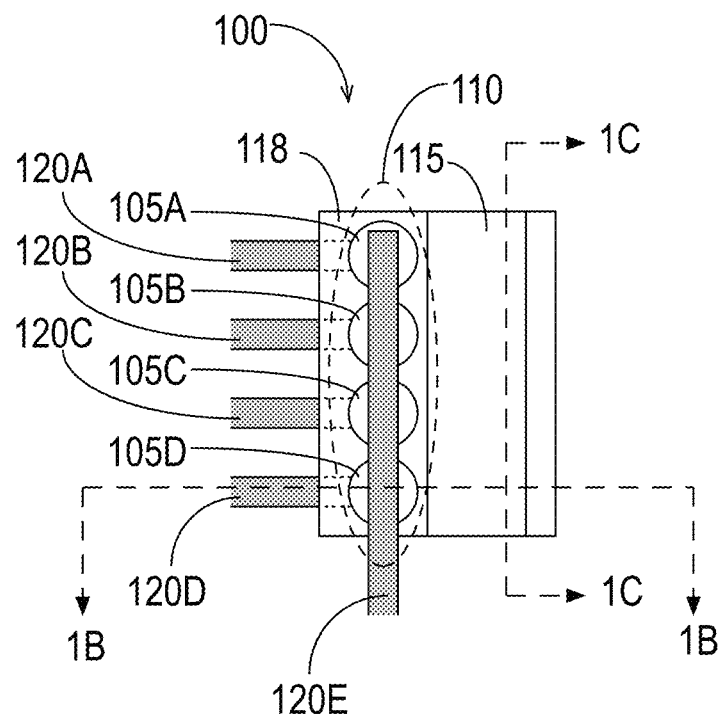
FIGS. 1A, 1B, and 1C illustrate an exemplary detection device in accordance with some embodiments.

For simplicity of description, the disclosure below will use DNA for illustration and discussion, though various embodiments can be generally applied to molecule detection.

The use of magnetic nanoparticles (MNPs) for molecule detection, such as for nucleic acid sequencing (e.g., DNA sequencing) has been proposed as an alternative to the use of fluorescent labels. See, for example, U.S. application Ser. No. 16/791,759, filed Feb. 14, 2020 and entitled "SPIN TORQUE OSCILLATOR (STO) SENSORS USED IN NUCLEIC ACID SEQUENCING ARRAYS AND DETECTION SCHEMES FOR NUCLEIC ACID SEQUENCING", which published as U.S. 2020/0324283 on Oct. 15, 2020; U.S. application Ser. No. 16/819,636 filed Mar. 16, 2020 and entitled "DEVICES AND METHODS FOR FREQUENCY- AND PHASE-BASED DETECTION OF MAGNETICALLY-LABELED MOLECULES USING SPIN TORQUE OSCILLATOR (STO) SENSORS", which published as U.S. 2020/0326392 on Oct. 15, 2020; U.S. application Ser. No. 16/727,064, filed Dec. 26, 2019 and entitled "DEVICES AND METHODS FOR MOLECULE DETECTION BASED ON THERMAL STABILITIES OF MAGNETIC NANOPARTICLES", which published as U.S. 2020/0326309 on Oct. 15, 2020; U.S. application Ser. No. 16/697,013, filed Nov. 26, 2019 and entitled "THERMAL SENSOR ARRAY FOR MOLECULE DETECTION AND RELATED DETECTION SCHEMES", which published as U.S. 2020/0326335 on Oct. 15, 2020 and issued as U.S. Pat. No. 11,327,073 on May 10, 2022; and U.S. application Ser. No. 16/659,383, filed Oct. 21, 2019 and entitled "MAGNETORESISTIVE SENSOR ARRAY FOR MOLECULE DETECTION AND RELATED DETECTION SCHEMES", which published as U.S. 2020/0326391 on Oct. 15, 2020 and issued as U.S. Pat. No. 11,112,468 on Sep. 7, 2021. All of the above-referenced applications are hereby incorporated by reference in their entireties for all purposes.

In one approach for DNA sequencing applications that uses magnetic nanoparticles as labels, four nucleotide precursors, each labeled by a different MNP type, may be used to sequence many (e.g., millions of) clusters of DNA strands in parallel. As in conventional approaches, DNA polymerase catalyzes the incorporation of dNTPs into a DNA template strand during sequential cycles of DNA synthesis. In contrast to conventional approaches, however, the dNTPs are magnetically-labeled. In each sequencing cycle, the bound double strand DNA molecule is exposed to DNA polymerase and a mixture of the four magnetically-labeled 3'-blocked NTPs. The polymerase adds one of the four dNTPs to the growing oligonucleotide chain (whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA. Because only one of the four types of dNTP will have been added to each oligonucleotide, and the four magnetic labels are distinguishable, the identity of the incorporated dNTP can be identified using various types of sensors and detection circuitry disclosed, for example, in U.S. application Ser. Nos. 16/791,759, 16/819,636, 16/727,064, 16/697,013, and 16/659,383.

In another approach, all of the nucleotide precursors are labeled by the same type of MNP, and only one of the four magnetically-labeled nucleotide precursors is tested at a time. After each nucleotide precursor is added, the polymerase adds a dNTP to oligonucleotide chains in which the next unpaired base is the one that is complementary to the magnetically-labeled dNTP that was added. Because the identity of the added nucleotide precursor is known, it is possible to determine, based on signals sensed by the sensors, the last-completed base of each of the ssDNA strands that has incorporated the magnetically-labeled dNTP.

A number of sensor embodiments have been disclosed (see, e.g., U.S. application Ser. Nos. 16/791,759, 16/819,636, 16/727,064, 16/697,013, and 16/659,383). These sensors may be, for example, sensors that sense heat generated by the MNPs when they are exposed to an alternating magnetic field (disclosed, e.g., in U.S. application Ser. No. 16/697,013 and Ser. No. 16/727,064). As another example, each of sensors may be a magnetoresistive (MR) sensor (e.g., a magnetic tunnel junction (MTJ)), the resistance of which changes depending on whether a MNP is in its vicinity (disclosed, e.g., in U.S. application Ser. No. 16/659,383). As yet another example, the sensors may use spin-torque oscillators (STDs), spin valves, or similar structures that generate a radio-frequency (RF) signal in response to a MNP being is in the vicinity (disclosed, e.g., in U.S. application Ser. No. 16/791,759 and Ser. No. 16/819,636). In such embodiments, the presence or absence of a MNP in the vicinity of a sensor may be determined by sensing, for example, the presence or absence of a RF signal generated by the STO, or the frequency (or variation in frequency), phase (or variation in phase), or noise of a RF signal generated by the STO. Other types of sensors (e.g., optical sensors) are possible and are contemplated. The examples provided herein are not intended to be limiting.

Figure 1B:
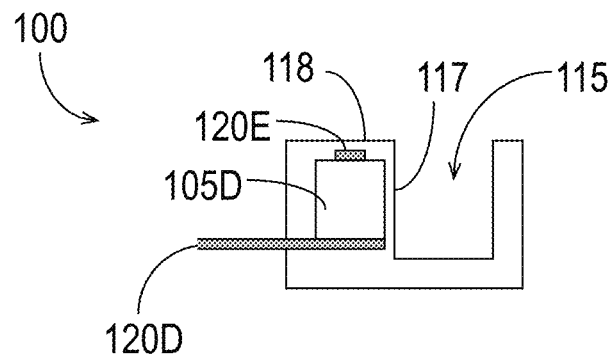
Figure 1C:
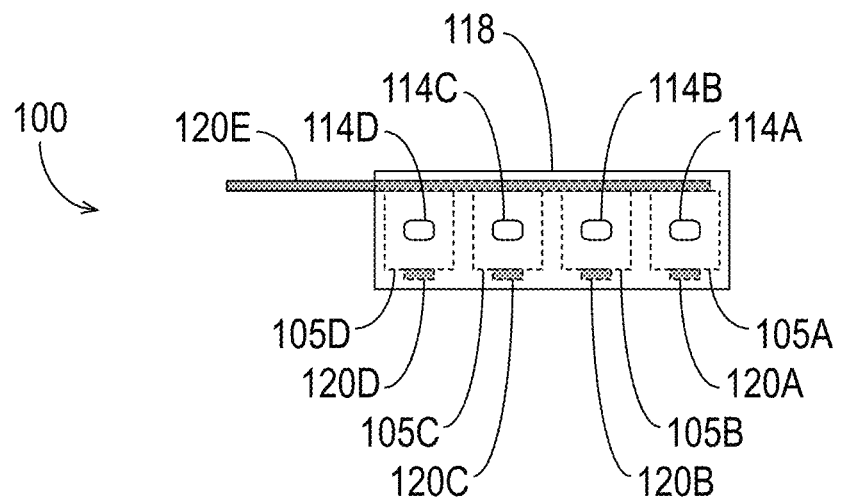

Devices for use in molecule detection based on MNPs have been disclosed in the above-referenced patent applications. FIGS. 1A, 1B, and 1C illustrate an exemplary detection device 100 in accordance with some embodiments. The exemplary detection device 100 includes a plurality of sensors 105 arranged in an array 110 disposed adjacent to a reagent area 115, illustrated in FIGS. 1A through 1C as a fluidic channel. FIG. 1A is a top view of the apparatus, FIG. 1B is a cross-section view at the position indicated by the dashed line labeled "1B" in FIG. 1A, and FIG. 1C is another cross-section view at the position indicated by the dashed line labeled "1C" in FIG. 1A. The sensors 105 may be any sensors able to detect the presence or absence of MNPs in the reagent area 115, some examples of which were described above. It is to be understood that although FIGS. 1A, 1B, and 1C illustrate an exemplary device that includes multiple sensors 105, an embodiment may have as few as one sensor 105.

As shown in FIG. 1A, the exemplary detection device 100 comprises a sensor array 110 that includes a plurality of sensors 105, with four sensors 105A, 105B, 105C, and 105D shown. (For simplicity, this document refers to sensors by the reference number 105. Individual sensors are designated by the reference number 105 followed by a letter.) It is to be understood that the detection device 100 may include more or fewer than four sensors 105. The sensor array 110 illustrated in the exemplary embodiment of FIG. 1A is a linear array.

In some embodiments, each of the plurality of sensors 105 is coupled to at least one line 120 for reading a characteristic of one or more of the sensors 105. (For simplicity, this document refers to lines by the reference number 120. Individual lines are designated by the reference number 120 followed by a letter.) The characteristic provides an indication of whether one or more MNPs are in the vicinity of a sensor 105. For example, as stated above and in the applications incorporated by reference, the characteristic may be a temperature or a change in temperature, a resistance or change in resistance, a voltage or change in voltage, a current or change in current, a presence or absence of a RF signal, a feature of a RF signal (e.g., phase, noise, frequency), a change in an aspect of an RF signal (e.g., its phase, noise, frequency), or any other characteristic that indicates whether one or more MNPs are in the vicinity of the sensor 105.

In the exemplary embodiment shown in FIG. 1A, each sensor 105 of the sensor array 110 is coupled to two lines 120. Specifically, the sensor 105A is coupled to the lines 120A and 120E, the sensor 105B is coupled to the lines 120B and 120E, the sensor 105C is coupled to the lines 120C and 120E, and the sensor 105D is coupled to the lines 120D and 120E. In the exemplary embodiment, the lines 120A, 120B, 120C, and 120D reside under the sensors 105A, 105B, 105C, and 105D, respectively, and the line 120E resides over the sensors 105. FIG. 1B shows the sensor 105D in relation to the lines 120D and 120E.

The detection device 100 also includes a reagent area 115 that is adjacent to the sensor array 110. As its name suggests, the reagent area 115 is configured to hold reagents (e.g., fluids such as liquids, gases, plasmas) when the detection device 100 is in use. The reagent area 115 may have any suitable shape (regular or irregular) to hold fluids, and it may include at least one movable piece (e.g., a stopper, a flap, etc.) to allow reagents to enter into and/or exit the reagent area 115. In the exemplary embodiment shown in FIGS. 1A through 1C, the reagent area 115 is a fluidic channel. The reagent area 115 may include or may be coupled to a pump or similar device that forces fluids into and/or out of the reagent area 115 (e.g., through a membrane, opening, etc.). It is to be understood that although FIGS. 1A through 1C illustrate the detection device 100 including the reagent area 115, the detection device 100 is not required to include the reagent area 115. For example, the detection device 100 may, in some embodiments, be mounted on a needle and inserted into a subject (e.g., a person, an animal, etc.) to test the subject's blood in vivo. In such an embodiment, the subject's blood vessel would serve as the reagent area 115.

As shown in FIG. 1B, the reagent area 115 has a wall 117 that is adjacent to the sensor array 110. The wall 117 has properties and characteristics that protect the sensors 105 from whatever fluid is in the reagent area 115 while still allowing the sensors 105 to detect MNPs that are within the reagent area 115 near the sensors 105. For example, the material of the wall 117 (and potentially of the rest of the reagent area 115) may be or comprise an insulator or metal (e.g., polypropylene, gold, glass, silicon, etc.). The thickness of the wall 117 may be selected so that the sensors 105 can detect MNPs within the reagent area 115. The wall 117 may be, for example, between approximately 2 nm and approximately 20 nm thick. In general, the reagent area 115 and wall 117 may have any shapes that allow the sensors 105 to detect the presence of MNPs near or attached to the wall 117, within the reagent area 115.

FIG. 1C is a cross-section view of the detection device 100 along the dashed line labeled "1C" in FIG. 1A. Because the cross-section is taken at a point within the reagent area 115, the sensors 105 and lines 120 would not be visible and are, therefore, shown using dashed lines to illustrate their positions within the detection device 100. As shown in FIG. 1C, in some embodiments, the wall 117 has a support structure 114 (or multiple support structures 114) configured to anchor molecules to be sensed (e.g., nucleic acids or molecules of a nucleic acid polymerase) to the wall 117 near the sensors 105. (For simplicity, this document refers to support structures by the reference number 114. Individual support structures are designated by the reference number 114 followed by a letter.) FIG. 1C illustrates four individual support structures 114A, 114B, 114C, and 114D, each of which corresponds to a respective sensor 105 (e.g., support structure 114A corresponds to sensor 105A, support structure 114B corresponds to sensor 105B, etc.). The support structure 114 (or support structures 114) of the wall 117 may include a cavity or a ridge to which molecules (e.g., nucleic acids, polymerase, etc.) may be attached or anchored. Although FIG. 1C shows individual support structures 114 corresponding to each of the sensors 105, the detection device 100 may have fewer or more support structures 114 than shown. For example, there may be more support structures 114 than sensors 105, such that each sensor 105 is near multiple support structures 114. As another example, multiple sensors 105 may share a single support structure 114. As yet another example, multiple sensors 105 may share multiple support structures 114. In embodiments in which the detection device 100 includes multiple support structures 114, those support structures 114 may be the same as or similar to each other, or some or all of them may be different from each other.

In some embodiments, it may be advantageous for each sensor 105 to detect MNPs coupled to a single respective support structure 114. For example, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, distinct sub-strands (e.g., ATGG and CTTAG) as well as, if a plurality of the longer strands are cut into sub-strands, sub-strands that partially or completely overlap other sub-strands (e.g., TGGC and GCTTA). All of the smaller, randomized sub-strands may be sequenced at the same time, potentially after being amplified. In such applications, it will be appreciated that because the sub-strands do not represent the same sub-sequences, it may be desirable to detect, independently and for each sensor 105, a characteristic (or change in a characteristic) caused by MNPs being in the vicinity of that sensor 105 because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it is desirable, in each sequencing cycle, to determine whether and at which physical location(s) each dNTP type has been incorporated.

To simplify the explanation, FIGS. 1A, 1B, and 1C illustrate an exemplary detection device 100 with a single reagent area 115 and only four sensors 105A, 105B, 105C, 105D in the sensor array 110. It is to be appreciated that the detection device 100 may have many more sensors 105 in the sensor array 110, and it may have either additional reagent areas 115 or a more intricate single reagent area 115 (e.g., with a different shape or with interconnected channels). In general, any configuration of sensors 105 and reagent area(s) 115 that allows, for each sensor 105, detection of a characteristic (or change in a characteristic) caused by MNPs being in the vicinity of that sensor 105 in the reagent area(s) 115 may be used.

Furthermore, it is to be understood that although FIGS. 1A through 1C illustrate a detection device 100 having sensors 105 disposed to detect molecules coupled to a wall 117 of the reagent area 115, other configurations are possible. For example, in DNA sequencing applications, it is possible to have a sensor 105 at or near the center of (for example) a cluster or circle of DNA strands.

Figure 1D:
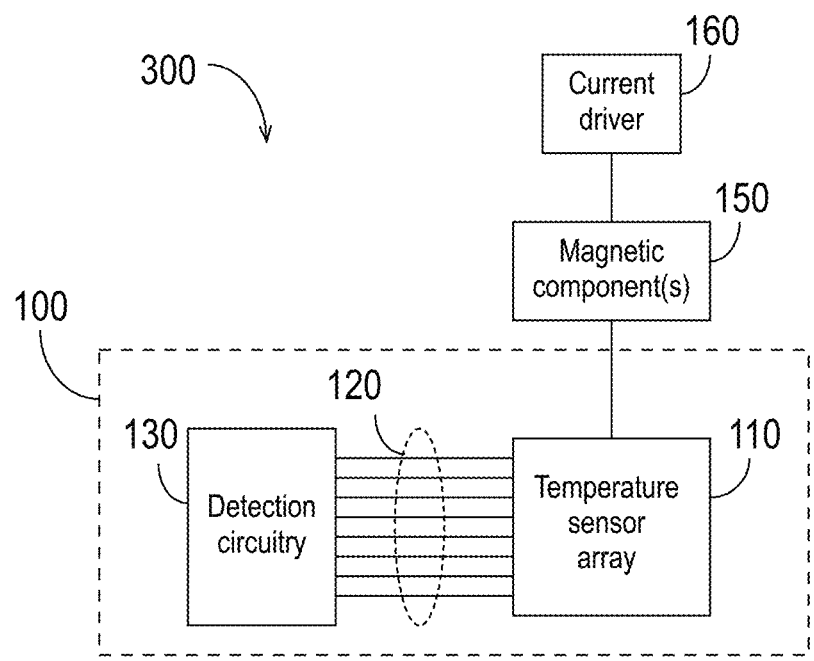
FIG. 1D is a block diagram showing an exemplary detection system for molecule detection in accordance with some embodiments.

FIG. 1D is a block diagram showing an exemplary detection system 300 for molecule detection in accordance with some embodiments. As illustrated in FIG. 1D, the system 300 includes a detection device 100 (as shown, comprising detection circuitry 130 coupled to the sensor array 110 via the lines 120). As also shown in FIG. 1D, the detection system 300 may also include one or more magnetic components 150, and/or a current driver 160 coupled to the magnetic component(s) 150. The magnetic component(s) 150 may comprise, for example, an electromagnet, a distributed coil, a solenoid, a permanent magnet, or a superconducting magnet, which may be used to generate a magnetic field as described in further detail below. In some embodiments, the magnetic component(s) 150 comprise an electromagnet, which may be advantageous because the magnetic field can be switched off. In other embodiments, the magnetic component(s) 150 comprise a permanent magnet.

As an example of a detection device 100 with a larger number of sensors 105 in the sensor array 110, FIGS. 1E, 1F, 1G, and 1H illustrate that includes several reagent areas 115, one or more of which may be a separate reagent area 115 in accordance with some embodiments, or the aggregation of which may be considered a single reagent area 115. In the embodiment of the detection device 100 shown in FIGS. 1E, 1F, 1G, and 1H, the plurality of sensors 105 of the sensor array 110 is arranged in a rectangular grid pattern that forms a cross-point array. Each of the lines 120 identifies a row or a column of the sensor array 110. It is to be understood that the terms "row" and "column" refer generally to the two dimensions of a rectangular grid of sensors 105, but the designation of which dimension constitutes rows and which constitutes columns is arbitrary. It is also to be understood that FIGS. 1E, 1F, 1G, and 1H show only a portion of the detection device 100 to avoid obscuring the parts of the detection device 100 being discussed. It is to be understood that the various illustrated components (e.g., lines 120, sensors 105, reagent areas 115, etc.) might not be visible in a physical instantiation of the detection device 100 (e.g., some or all may be covered by protective material, such as an insulator material).

Figure 1E:
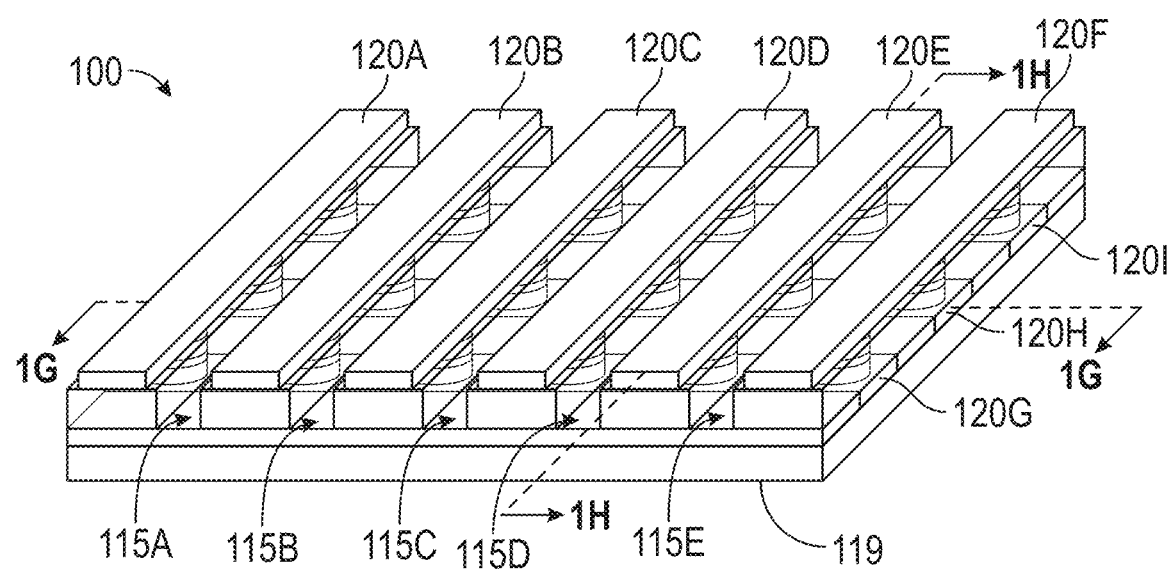
FIGS. 1E, 1F, 1G, and 1H illustrate portions of an exemplary detection device in accordance with some embodiments

FIG. 1E is a perspective view of the exemplary detection device 100 in accordance with some embodiments. The detection device 100 includes nine lines 120, labeled as 120A, 120B, 120C, 120D, 120E, 120F, 120G, 120H, and 120I. It also includes five reagent areas, labeled as 115A, 115B, 115C, 115D, and 115E. As explained above, the reagent areas 115A, 115B, 115C, 115D, and 115E may be considered to be separate reagent areas 115 or a single reagent area 115. The detection device 100 also has a bottom surface 119.

Figure 1F:
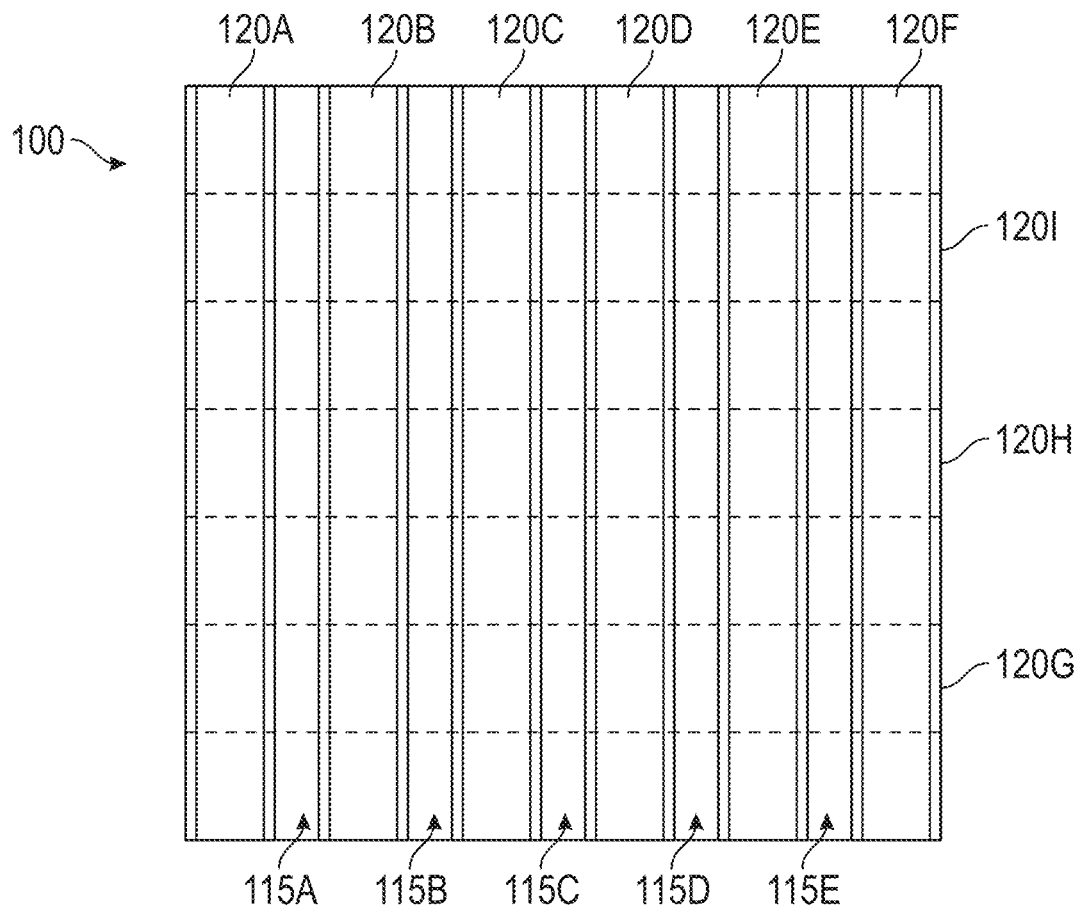

FIG. 1F is a top view of the exemplary detection device 100 from FIG. 1E. The lines 120G, 120H, and 120I, which are not visible from the top view, are shown using dashed lines to indicate their locations. The lines 120A-120F are shown in solid lines but, as explained above, the lines 120A-120F might also not be visible in the top view (e.g., they may be covered by protective material, such as an insulator material).

Figure 1G:
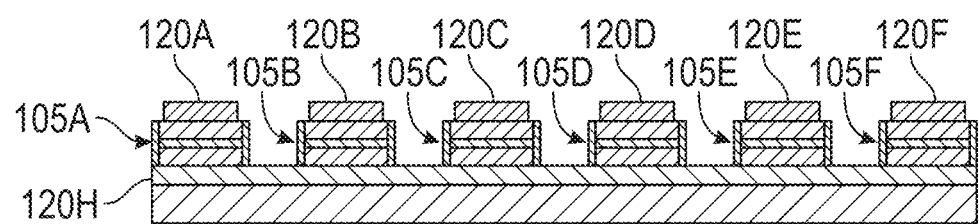

FIG. 1G is a cross-sectional view of the detection device 100 along the line labeled "1G" in FIG. 1E. As shown, each of the lines 120A, 120B, 120C, 120D, 120E, and 120F is in contact with the top of one of the sensors 105 along the cross-section (namely, line 120A is in contact with sensor 105A, line 120B is in contact with sensor 105B, line 120C is in contact with sensor 105C, line 120D is in contact with sensor 105D, line 120E is in contact with sensor 105E, and line 120F is in contact with sensor 105F). The line 120H is in contact with the bottom of each of the sensors 105A, 105B, 105C, 105D, 105E, and 105F. It is to be appreciated that although FIGS. 1E-1H illustrate the lines 120 in contact with the sensors 105, the lines 120 may, in general, be coupled to the sensors 105 (i.e., they may be directly connected, or there may be intervening components disposed between the lines 120 and the sensors 105).

Figure 1H:
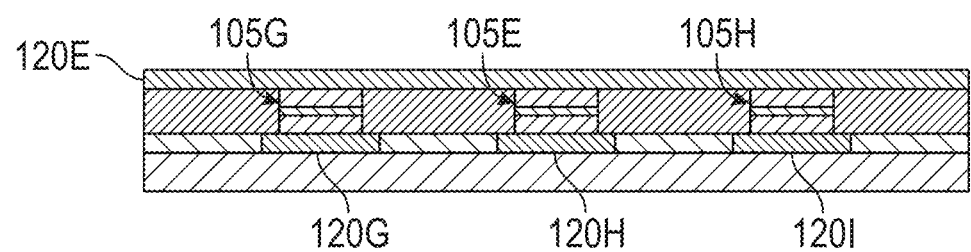

As illustrated in FIGS. 1E-1H, each of the lines 120 over the tops of the sensors 105 (top lines 120) is coupled to multiple of the lines 120 below the sensors 105 (bottom lines 120). For example, as shown in FIG. 1G, the line 120E, which resides above the sensor 105E, is coupled to the line 120H, which resides below the sensor 105E. The line 120H also resides below the sensors 105A, 105B, 105C, 105D, and 105F. As shown in FIG. 1H, the line 120E also resides over the sensors 105G and 105H. The sensor 105G is also coupled to the line 120G, which resides below the sensor 105G, and the sensor 105H is also coupled to the line 120I, which resides below the sensor 105I. Each of the sensors 105 can be selected by a unique pair of lines 120, one being a top line 120 and the other being a bottom line 120. Thus, when the sensors 105 are arranged in a cross-point configuration such as the exemplary configuration shown in FIGS. 1E-1H, a first top line 120 (a line 120 residing over the sensor array 110) is coupled to a first bottom line 120 (a line 120 residing below the sensor array 110) at a first location (corresponding to a sensor 105), and the first top line 120 is coupled to a second bottom line 120 at a second location (corresponding to a different sensor 105). Similarly, a second top line 120 is coupled to the first bottom line 120 at a third location (corresponding to yet another sensor 105), and the second top line 120 is coupled to the second bottom line at a fourth location (corresponding to yet another sensor 105). The first and second top lines 120 (which may select columns or rows of the sensor array 110) are substantially parallel to each other and substantially perpendicular to the first and second bottom lines 120. Similarly, the first and second bottom lines 120 are substantially parallel to each other and substantially perpendicular to the first and second top lines 120.

Referring to FIG. 1G, the sensors 105A and 105B are separated by the reagent area 115A (unlabeled in FIG. 1G but shown in FIG. 1E). Similarly, the sensors 105B and 105C are separated by the reagent area 115B, the sensors 105C and 105D are separated by the reagent area 115C, the sensors 105D and 105E are separated by the reagent area 115D, and the sensors 105E and 105F are separated by the reagent area 115E. As discussed further below, either or both of the vertical walls of each reagent area 115 may be the wall 117.

In some embodiments, each sensor 105 is assigned to a single reagent area 115. For example, in the exemplary device illustrated in FIGS. 1E-1H, the sensors 105 coupled to the line 120A may be configured to sense MNPs in the reagent area 115A, the sensors 105 coupled to the line 120B may be configured to sense MNPs in the reagent area 115B, the sensors 105 coupled to the line 120C may be configured to sense MNPs in the reagent area 115C, the sensors 105 coupled to the line 120D may be configured to sense MNPs in the reagent area 115D, and the sensors 105 coupled to the line 120E may be configured to sense MNPs in the reagent area 115E.

In the exemplary embodiment illustrated in FIGS. 1E-1H, there are more columns of sensors 105 than there are reagent areas 115 (i.e., in the exemplary embodiment shown, there are six columns corresponding to lines 120A-120F and only five reagent areas 115A-115E). In such embodiments, each vertical wall of one reagent area 115 may be the wall 117. In other words, a single reagent area 115 may be sensed by twice as many sensors 105 as each of the other reagent areas 115. For example, in the exemplary embodiment of FIGS. 1E-1H, any of the reagent areas 115 may be sensed by two columns of sensors 105. For example, the reagent area 115B may be sensed by the sensors 105 coupled to both lines 120B and 120C. In this example, the sensors 105 coupled to the line 120A would be assigned to sense the contents of the reagent area 120A, the sensors 105 coupled to the line 120D would be assigned to sense the contents of the reagent area 120C, the sensors 105 coupled to the line 120E would be assigned to sense the contents of the reagent area 120D, and the sensors 105 coupled to the line 120F would be assigned to sense the contents of the reagent area 120E.

FIG. 1H is a cross-sectional view of the detection device 100 along the line labeled "1H" in FIG. 1E. As shown, the line 120E is in contact with the top of each of the sensors 105G, 105E, and 105H along the cross-section. Each of the lines 120G, 120H, and 120I is in contact with the bottom of one of the sensors 105 along the cross-section (namely, line 120G is in contact with sensor 105G, line 120H is in contact with sensor 105E, and line 120I is in contact with sensor 105H). As explained above, the lines 120 shown in FIG. 1H need not be in direct contact with the sensors 105; instead, they may be connected through intervening components.

In some embodiments (see, e.g., FIGS. 1I, 1J), the detection device 100 includes one or more selector elements 111, each of which is coupled to a respective one of the one or more sensors 105, where each of the selector elements 111 exhibits thresholding behavior such that for voltages above a given value (i.e., $V_{th}$) the selector element 111 has high conductivity, and below that voltage the conductivity of the selector element 111 is effectively zero. The selector elements 111 may comprise, for example, transistors, diodes, etc. As will be appreciated by those having ordinary skill in the art, different schemes of addressing (selecting) the sensors 105 (individually or in groups) can be used that ensure only the voltage dropped across the intended sensor(s) 105 is above $V_{th}$. Accordingly, selector elements 111 may be used reduce the chances of "sneak" currents that could transmit through neighboring elements and degrade the performance of the detection device 100.

Figure 1I:
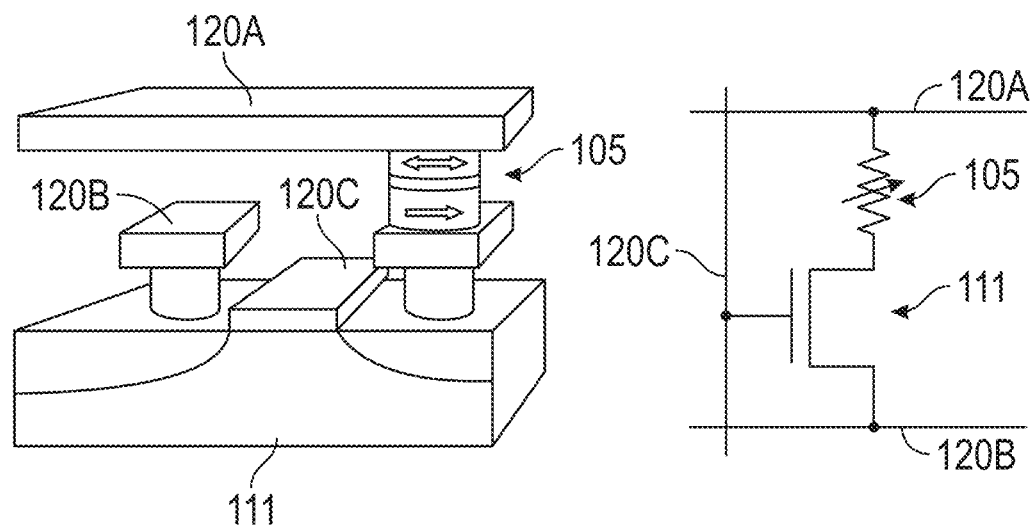
FIGS. 1I and 1J illustrate exemplary sensor selection approaches in accordance with some embodiments.

FIG. 1I illustrates an exemplary sensor 105 selection approach in accordance with some embodiments. In the exemplary embodiment shown in FIG. 1I, a respective selector element 111 (e.g., shown as a CMOS transistor) is coupled in series with the sensor 105. In this exemplary embodiment, three lines 120A, 120B, and 120C allow a characteristic of the sensor 105 to be sensed. Conceptually, the line 120A may be considered to be a read-out line, the line 120C may be considered to be a control line, and the line 120B may be considered to be either or both a read-out line and a control line. For more detail on configurations such as the exemplary one shown in FIG. 1I, see B. N. Engel, J. Åkerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAM Based on a Novel Bit and Switching Method," IEEE Transactions on Magnetics, Vol. 41, 132 (2005).

Figure 1J:
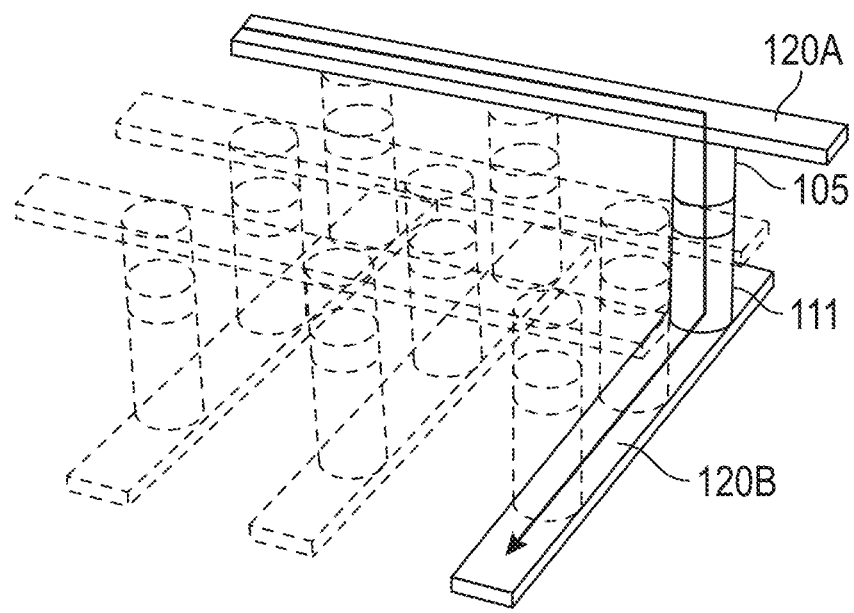

FIG. 1J illustrates another exemplary sensor 105 selection approach in accordance with some embodiments. In the exemplary embodiment shown in FIG. 1J, a selector element 111 (e.g., a diode or a similar thresholding element, as is known in the art, such as semiconductor diodes, operational transconductance amplifiers (OTAs), vanadium oxide layers, capacitive threshold-logic gates, etc.) is deposited "in-stack" together with the magnetic films of the sensors 105 and then placed into a cross-point architecture. Although FIG. 1J shows the in-stack selector elements 111 below the sensors 105, it is to be understood that the order of the in-stack selector elements 111 and the sensors 105 may be reversed. Respective selector devices (e.g., CMOS transistors) may be used to turn on the individual lines 120A, 120B to address/access individual sensors 105 in the detection device 100. The use of CMOS select transistors may be simple due to the prevalence of foundries available to fabricate the front end (i.e., the nanofabrication to build the CMOS transistors and underlying circuitry), but the types of currents used for operation may use a cross-point design to eventually reach the densities desired. Additional details on configurations suitable to select sensors 105 (e.g., in cross-point arrays) may be found in C. Chappert, A. Fert, and F. N. Van Daul, "The emergence of spin electronics in data storage," Nature Materials, Vol. 6, 813 (2007) and in J. Woo et al., "Selector-less RRAM with non-linearity of device for cross-point array applications," Microelectronic Engineering 109 (2013) 360-363.

Figure 2A:
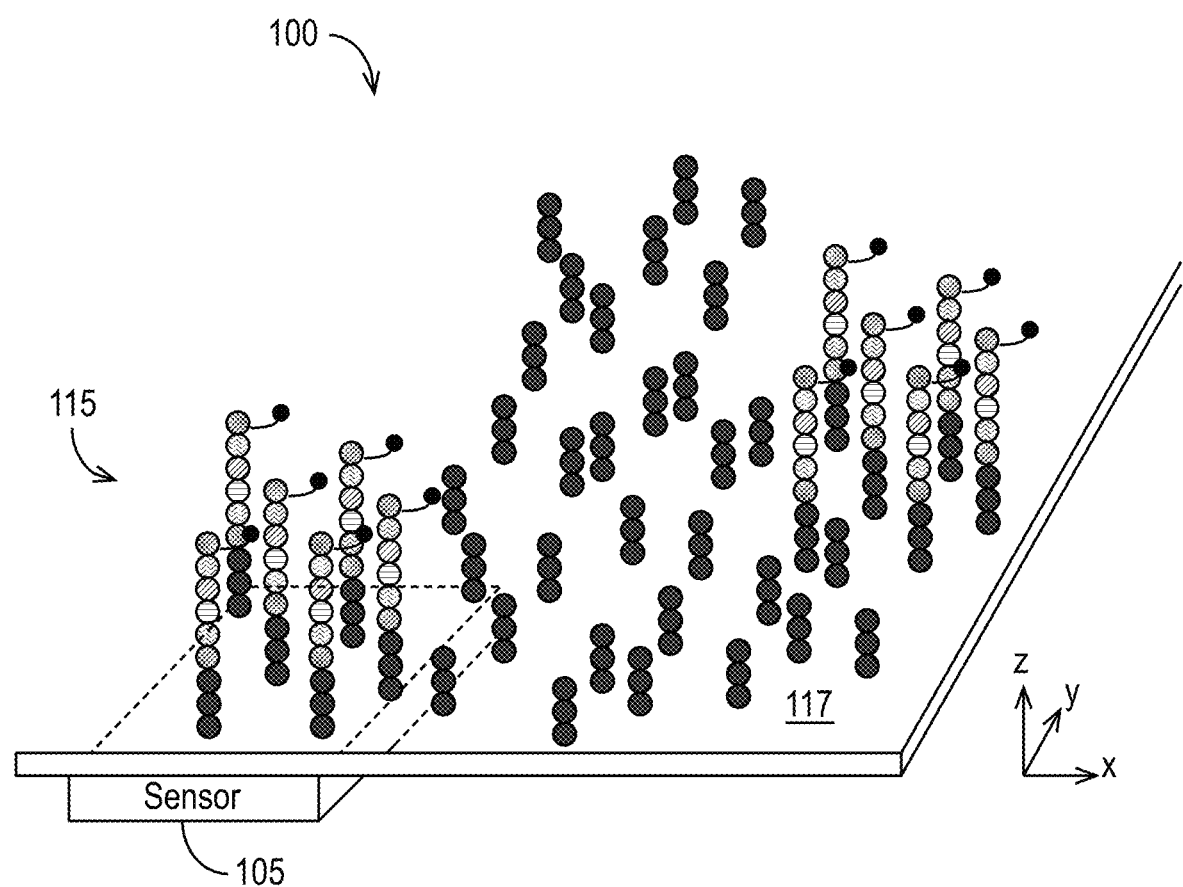
FIG. 2A illustrates DNA template strands distributed over a two dimensional area on or around an exemplary support structure following an amplification procedure in accordance with some embodiments.
Figure 2B:
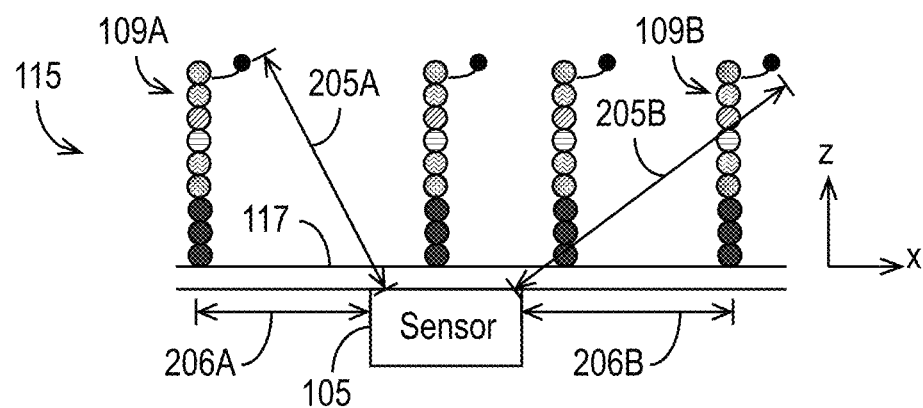
FIG. 2B illustrates an exemplary sensor with DNA strands, each having a MNP label attached to the last dNTP incorporated into the target DNA strand in accordance with some embodiments.

One consequence of PCR amplification for approaches using MNPs and detection devices 100 such as the exemplary detection devices 100 illustrated in FIGS. 1A-1H is that the resulting cluster of DNA template strands can be spread out over a two dimensional area on or around the support structure(s) 114 (e.g., on the wall 117) within the reagent area 115, as illustrated in FIG. 2A. Typically, following the PCR amplification procedure, the DNA template strands are around 40 nm apart from each other. Moreover, as the sequencing protocol proceeds, the DNA strands grow longer. Thus, as each nucleotide precursor labeled by a MNP is incorporated, the distance between the sensor 105 and the MNP label of the last-incorporated nucleotide precursor also increases. FIG. 2B illustrates a sensor 105 and four DNA strands, each having a MNP label attached to the last dNTP incorporated into the target DNA strand. The attachment location of the DNA strand 109A on the support structure 114 of the wall 117 (or elsewhere within the reagent area 115) is at a lateral distance 206A from the sensor 105. The MNP is a distance 205A from the sensor 105. Similarly, the attachment location of the DNA strand 109B is on the support structure 114 of the wall 117 (or elsewhere within the reagent area) is at a lateral distance 206B from sensor 105, and its MNP is a distance 205B from the sensor 105.

Depending on the distances between the MNPs and the sensors 105, MNPs labeling dNTPs incorporated into a DNA template strand attached to the support structure 114 near a particular sensor 105 may be too far away for the sensor 105 to detect them reliably. It would be desirable for the MNPs to be closer to the sensors 105 to improve the detection probability and signal-to-noise ratio (SNR) of the detection procedure.

Disclosed herein are devices and methods for reducing the distances between MNPs labeling the molecules being detected and the sensors 105 that detect those MNPs. Generally, the MNPs are moved closer to the sensors 105 by an applied magnetic field, which causes a gradient that draws the MNPs toward the area with the largest gradient, near the sensor 105.

Figure 3:
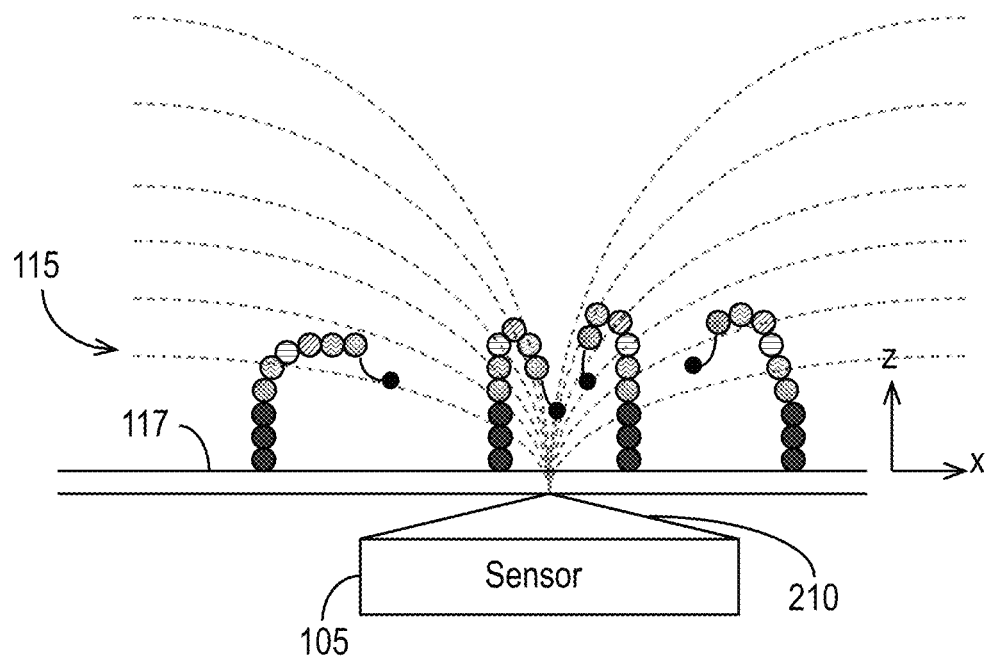
FIG. 3 illustrates an exemplary pole piece for generating a magnetic field in accordance with some embodiments.

FIG. 3 is an example that illustrates the operating principle of at least some of the disclosed embodiments, and is not intended to limit them. A pole piece 210, which acts as a field concentrator, is coupled to the sensor 105 and disposed between the sensor 105 and the wall 117. The pole piece 210 emits a magnetic field (shown as curved dashed lines) that has the largest gradient close to the sensor 105. The gradient draws the MNPs toward the sensor 105, thereby reducing the distances between the MNPs and that sensor 105. The pole piece 210 may be connected to or may include, for example, lines 120. The pole piece 210 may be made of any suitable material, such as, for example, a magnetic material (e.g., FeNi alloy, etc.). For example, the pole piece 210 may comprise permalloy (a nickel iron magnetic alloy) or any other material having a high magnetic permeability and low coercivity. The shape of the pole piece 210 shown in FIG. 3 is an example illustration. The shape can be different, as explained further below.

Figure 4A:
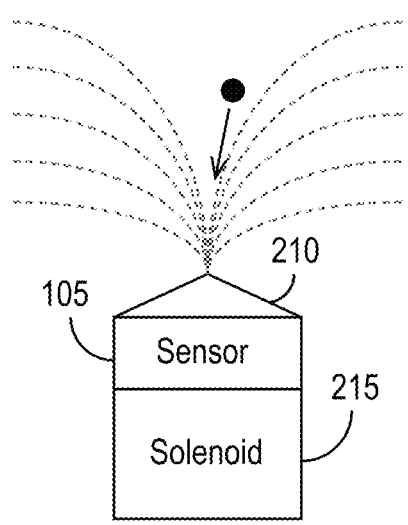
FIG. 4A illustrates a sensor coupled to and disposed between a solenoid and a cone-shaped pole piece in accordance with some embodiments.

The magnetic field can be generated in a number of ways beyond the example pole piece shown in FIG. 3. FIG. 4A illustrates one exemplary embodiment in which the sensor 105 is coupled to and disposed between a solenoid 215 and a cone-shaped pole piece 210. The applied magnetic field draws the MNPs toward the tip of the pole piece 210 as shown in FIG. 4A. It is to be appreciated that FIG. 4A shows the pole piece 210 in cross section, and that the three-dimensional pole piece 210 may have, for example, a pyramidal shape or any other shape that is conducive to directing or concentrating a magnetic field. For example, the pole piece 210 may comprise an edge or point. It is also to be appreciated that although FIG. 4A illustrates a solenoid 215, that solenoid 215 may alternatively be a ferromagnetic component, such as, for example, a ferromagnet, as explained in further detail below.

Figure 4B:
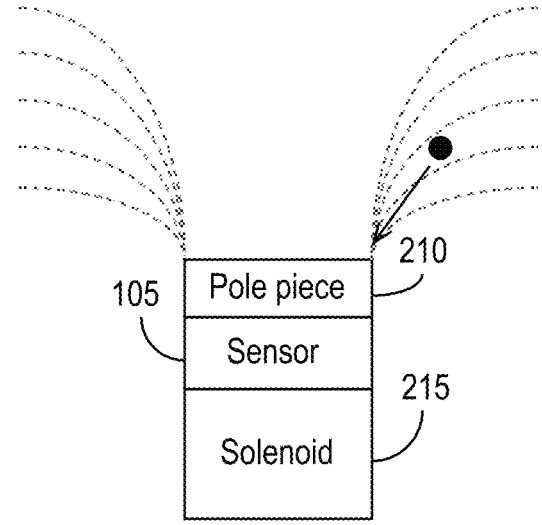
FIG. 4B illustrates a sensor coupled to and disposed between a solenoid and a rectangular pole piece in accordance with some embodiments.

FIG. 4B illustrates another exemplary embodiment in which the sensor 105 is coupled to and disposed between a solenoid 215 and a rectangular pole piece 210. The applied magnetic field draws the MNPs toward the edges of the rectangular pole piece 210.

Figure 4C:
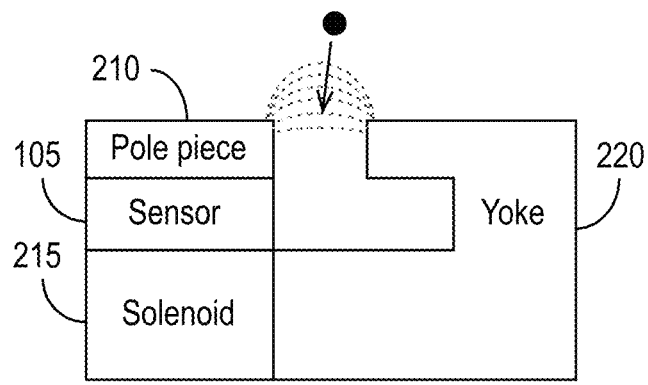
FIG. 4C illustrates a sensor coupled to and disposed between a solenoid and a pole piece in accordance with some embodiments.

FIG. 4C illustrates yet another exemplary embodiment in which the sensor 105 is coupled to and disposed between a solenoid 215 and a pole piece 210. In the exemplary embodiment of FIG. 4C, the solenoid 215 is coupled to a yoke 220, which may improve the sensitivity of the sensor 105. The pole piece 210 is functionally similar to a write pole of a magnetic recording write head used in a hard disk drive, and the yoke 220 is functionally similar to a return path of a magnetic recording write head. The magnetic field, which is similar to the write field of a magnetic recording write head, draws the MNPs toward the gap between the pole piece 210 and the yoke 220, which has a magnetic field gradient. The MNP changes the reluctance as it moves toward the gap. In this sense, the MNP acts similarly to a switch in the magnetic circuit formed by the yoke 220, the pole piece 210, the sensor 105, and the solenoid 215. For example, when the MNP is near or in the gap, it operates similarly to a closed switch.

In some embodiments, the magnetic field is selectively switched on and off depending on whether it is desirable to draw MNPs into the gap between the pole piece 210 and the yoke 220. For example, when the magnetic field is on, MNPs are drawn into the gap between the pole piece 210 and the yoke 220, thereby drawing them closer to the sensor 105. When the magnetic field is off, the MNPs are not drawn into the gap, and they may be washed away (e.g., between sequencing cycles).

As described above, FIG. 4C shows an exemplary embodiment that uses a solenoid 215. Other embodiments replace the solenoid 215 by a magnet (e.g., a ferromagnet), which does not need wiring and may be less expensive and/or simpler to manufacture than a solenoid 215. In some embodiments, for example, the yoke 220 is made out of a soft magnetic material, and a ferromagnet made of a material with some coercive field, but not a very hard magnetic material, replaces the solenoid 215 illustrated in FIG. 4C. An external magnetic field may be used to magnetize the ferromagnet to attract the MNPs into the gap between the pole piece 210 and the yoke 220. When the external magnetic field is switched off, the MNPs are no longer drawn into the gap. They may then be washed away (e.g., between sequencing cycles).

Figure 4D:
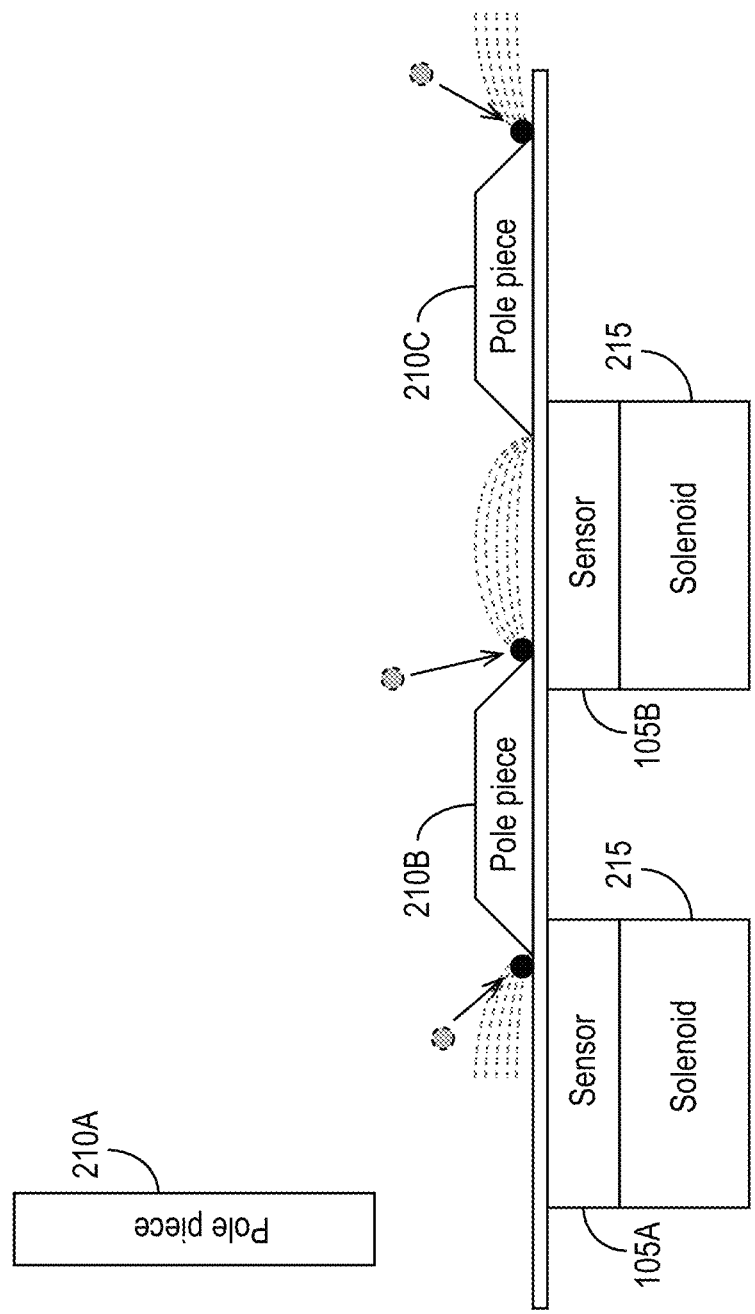
FIG. 4D illustrates exemplary configurations in which sensors are assisted by multiple pole pieces, and certain pole pieces assist multiple sensors in accordance with some embodiments.

In some embodiments, multiple sensors 105 may share a particular pole piece 210. Stated another way, a single pole piece 210 may assist multiple sensors 105. In addition or alternatively, a particular sensor 105 may be assisted by (e.g., it may sense MNPs directed toward it by) multiple pole pieces 210. Generally, a sensor 105 may be assisted by one or more pole pieces 210, and a pole piece 210 may assist one or more sensors 105. FIG. 4D illustrates some such exemplary configurations in which sensors 105 are assisted by multiple pole pieces 210, and certain pole pieces 210 assist multiple sensors 105. As shown in FIG. 4D, the sensor 105A is in the vicinity of two pole pieces, 210A and 210B. As shown, the pole piece 210A may be separated from the sensor 105A by some distance. The pole piece 210A may be, for example, attached to or formed by or on the back-side of the reagent area 115. The sensor 105A may also be assisted by one or more other pole pieces 210, such as, for example, the pole piece 210B. As shown in FIG. 4D, the pole piece 210B may be shared by the sensors 105A and 105B (and potentially by additional sensors 105). Similarly, the sensor 105B may be assisted by two or more pole pieces, namely the pole piece 210B (shown as being shared by sensor 105A) and the pole piece 210C (which may be shared by another sensor 105 (not illustrated)).

It is to be understood that the example embodiments shown in FIGS. 4A through 4D are merely illustrative. It will be appreciated that other structures having various shapes and sizes may be used as the pole piece 210. Also, structures other than a solenoid 215 and/or yoke 220 may be used alternatively or in addition. Furthermore, as shown in FIG. 4D and explained above, some of the structures (e.g., solenoid 215, yoke 220, pole piece 210, etc.) may be shared by more than one sensor 105.

Figure 5:
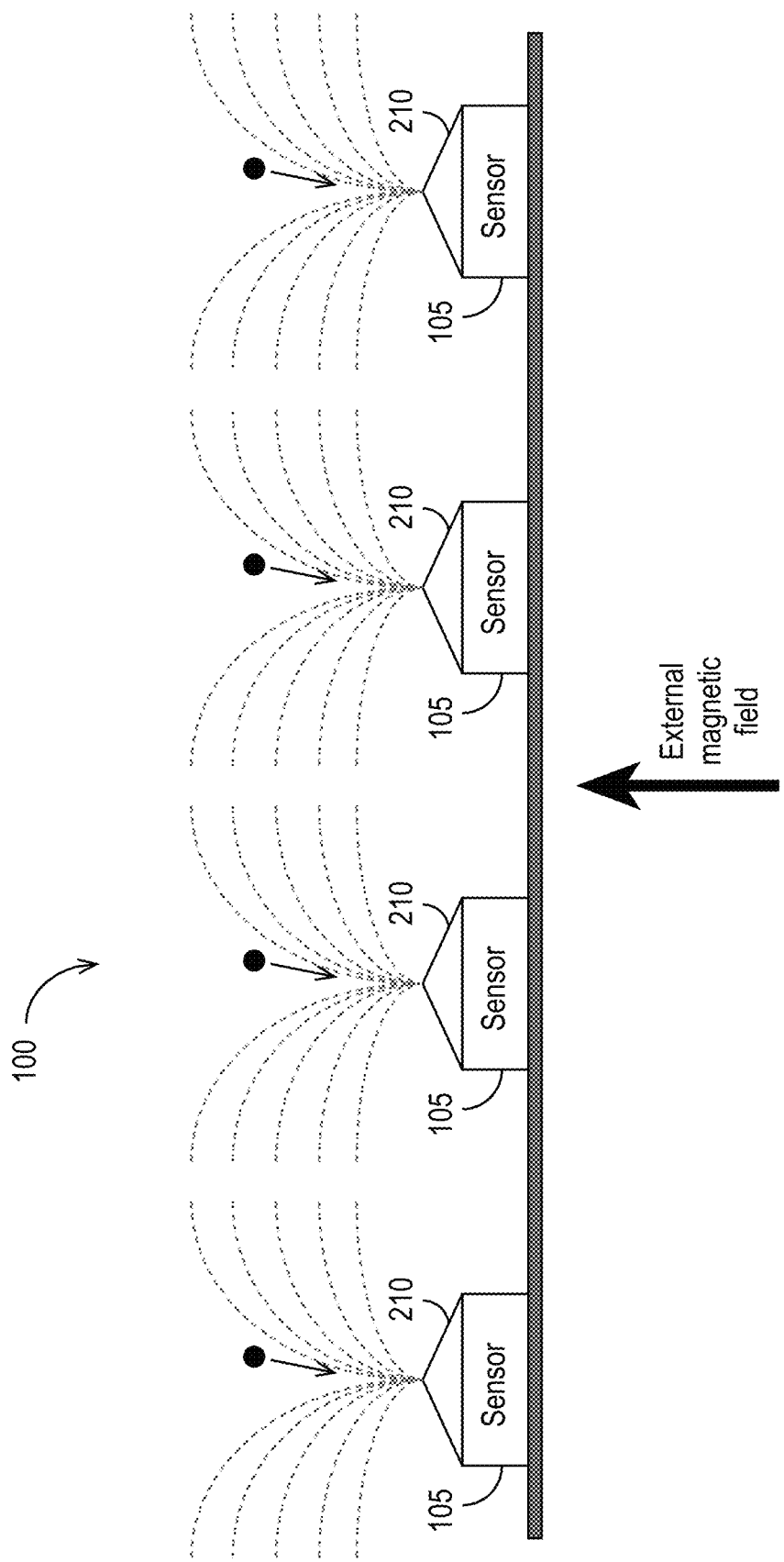
FIG. 5 illustrates an exemplary embodiment in which an external magnetic component is used to generate a magnetic field in accordance with some embodiments.

In some embodiments, instead of each sensor 105 being coupled to a solenoid 215, yoke 220, or similar structure, an external magnetic component (e.g., the magnetic component(s) 150 shown in FIG. 1D) is used to generate the magnetic field. FIG. 5 illustrates such an embodiment. The pole pieces 210 are illustrated as having triangular shapes (in cross-section), but, as explained above, the triangular shape is merely exemplary. Other shapes are possible (e.g., rectangular cross-sections, etc.) and are specifically contemplated.

The magnetic field may be adjusted to adapt to increasing distance between the sensor 105 and the MNPs coupled or attached to the support structure 114 assigned to that sensor 105. For example, in DNA sequencing applications, the distance between the MNPs and the sensor 105 will increase as the sequencing procedure proceeds and the DNA strands grow longer. To compensate, the magnetic field may be adjusted (increased) in later sequencing cycles relative to earlier sequencing cycles to move the MNPs over larger distances, closer to the sensors 105, to mitigate SNR degradation as the strands being sequenced grow longer.

Figure 6:
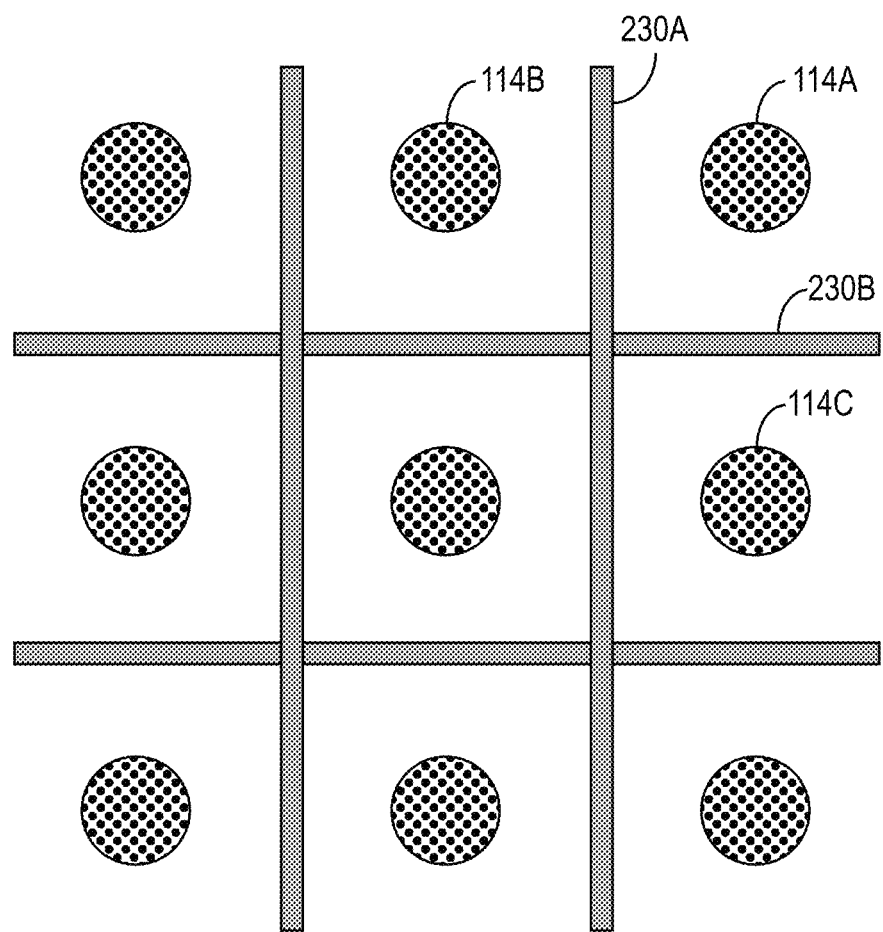
FIG. 6 is a conceptual view of an exemplary embodiment of a detection device that includes magnetic shields in accordance with some embodiments.

In some embodiments, magnetic shields are disposed between adjacent support structures 114 and/or sensors 105. FIG. 6 is a conceptual view of an exemplary embodiment of a detection device 100 that includes magnetic shields 230 shielding adjacent support structures 114 (and sensors 105) from each other in accordance with some embodiments. In the illustrated embodiment, the sensors 105 and support structures 114 are assumed to be in a one-to-one relationship. The magnetic shields 230 help to mitigate the likelihood that DNA strands coupled or attached to a particular support structure 114 will be drawn toward an adjacent sensor 105. For example, the magnetic shield 230A reduces the likelihood that a MNP attached to a nucleotide precursor incorporated in a DNA strand bound to the support structure 114A will be drawn toward the sensor 105 that is arranged to detect the presence of MNPs attached to nucleotide precursors incorporated in DNA strands bound to the support structure 114B. Similarly, the magnetic shield 230B reduces the likelihood that a MNP attached to a nucleotide precursor incorporated in a DNA strand bound to the support structure 114A will be drawn toward the sensor 105 that is arranged to detect the presence of MNPs attached to nucleotide precursors incorporated in DNA strands bound to the support structure 114C. When magnetic shields 230 are disposed between support structures 114, they can also restrict the area over which DNA strands to be detected by a particular sensor 105 are amplified.

Figure 7:
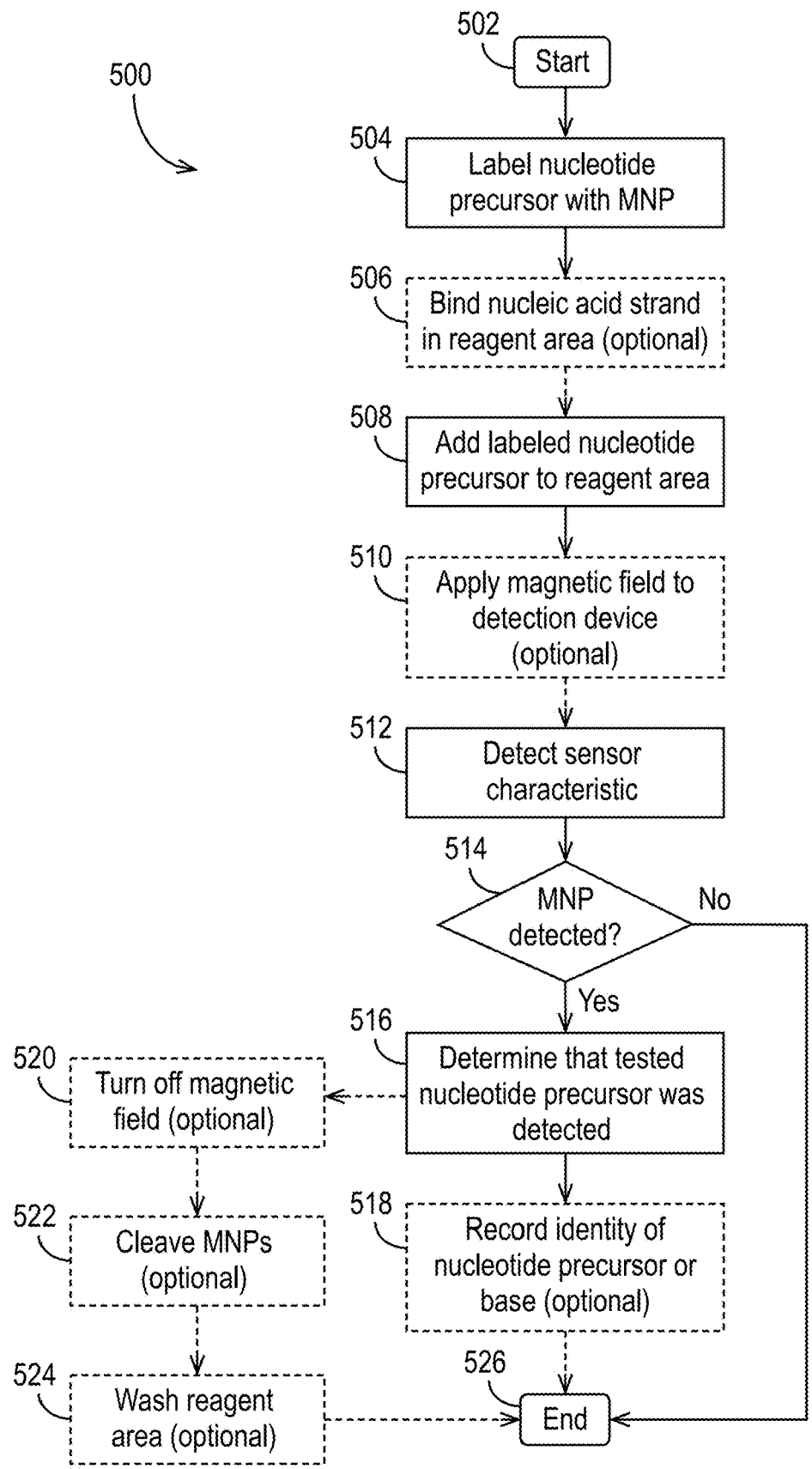
FIG. 7 illustrates an exemplary method of using a detection device for nucleic acid sequencing in accordance with some embodiments.

FIG. 7 illustrates an exemplary method 500 of using a detection device 100 for nucleic acid sequencing in accordance with some embodiments. At 502, the method 500 begins. At 504, a selected nucleotide precursor is magnetically-labeled using MNPs. At 506, a nucleic acid strand may optionally be bound to the detection device 100 in the reagent area 115. At 508, the magnetically-labeled nucleotide precursor is added to the reagent area 115. At 510, optionally, a magnetic field may be applied to the detection device (e.g., as described above in the context of FIGS. 3-5).

At 512, a characteristic of each of one or more sensors is detected. As explained above, the characteristic may be, for example, a voltage, current, resistance, frequency, phase, noise, or temperature; a change in voltage, current, resistance, frequency, phase, noise, or temperature; or a change in a statistical property (e.g., mean, variance, standard deviation, etc.) of voltage, current, resistance, frequency, phase, noise, or temperature. At 514, it is determined whether a MNP has been detected by a sensor 105. If not, then at 526, the method 500 ends. If so, then at 516, it is determined that the tested magnetically-labeled nucleotide precursor was detected. Optionally, at 518, the identity of the detected nucleotide precursor or, in DNA sequencing applications, the identity of the base that is complementary to the detected nucleotide precursor, may be recorded. Optionally, at 520, the magnetic field applied at step 510 may be turned off. Optionally, at 522, MNPs may be removed (e.g., cleaved from the nucleic acid strand bound to the detection device 100 in the reagent area 115). Optionally, at 524, the reagent area 115 may be washed to rinse away the removed MNPs and other residue before performing the method 500 again to test another nucleotide precursor or start a new detection cycle.

It is to be understood that FIG. 7 is merely exemplary. The method 500 may include steps that are not illustrated. For example, in DNA sequencing applications, polymerase may be added to the reagent area before detecting the sensor 105 characteristic, and/or additional washing steps may be performed (e.g., after step 508 and before step 512). Likewise, some of the steps can be performed in a different order, as will be appreciated by those having ordinary skill in the art. For example, the order of steps 504 and 506 could be swapped in FIG. 7. Accordingly, FIG. 7 is merely one illustration of how the detection device 100 may be used, and it is not intended to be limiting.

It is also to be appreciated that although the explanation of FIG. 7 refers only to a single nucleotide precursor, the method 500 may be used to test more than one nucleotide precursor at the same time if each type of nucleotide precursor is labeled by a different MNP type selected so that the characteristic detected by the sensors 105 allows the detection circuitry 130 to distinguish between the different MNP types. Methods allowing multiple nucleotide precursors to be detected during a single sequencing cycle have been disclosed in the applications incorporated by reference herein (e.g., U.S. application Ser. Nos. 16/791,759, 16/819, 636, 16/727,064, 16/697,013, and 16/659,383). The disclosures herein may be used in conjunction with those method embodiments (e.g., the method embodiments of U.S. application Ser. Nos. 16/791,759, 16/819,636, 16/727,064, 16/697,013, and 16/659,383 may be used with a detection device 100 that includes pole pieces 210 operable to draw MNPs toward the sensors 105, as disclosed herein). Similarly, it is to be understood that the method 500 shown in FIG. 7 can be performed more than once during a sequencing cycle (e.g., once per nucleotide precursor being tested if the same MNP type is used to label all nucleotide precursors being tested) as well as multiple times over the span of multiple sequencing cycles. For example, if the same MNP type labels each of four nucleotide precursors, the method 500 can be performed four times in a first sequencing cycle, then four more times in a second sequencing cycle, etc. As another example, if each of four nucleotide precursors is labeled by a different, distinguishable MNP type, the method 500 can be performed once during each sequencing cycle.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

The term "coupled" is used herein to express a direct connection/attachment as well as a connection/attachment through one or more intervening elements or structures. Accordingly, for example, with reference to FIG. 1I, lines 120B and 120C are coupled, as are lines 120B and 120A. Similarly, each of the lines 120A, 120B, and 120C is coupled to the sensor 105 (the line 120A directly, and the lines 120B and 120C through intervening elements (e.g., selector element 111)).

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature. The drawings are not necessarily to scale, and the dimensions, shapes, and sizes of the features may differ substantially from how they are depicted in the drawings.

It is to be understood that although parts of the disclosure are in the context of nucleic acid sequencing, and DNA sequencing in particular, the disclosures herein are applicable generally to the detection of molecules by using MNPs as tags or labels. It will be appreciated by those having skill in the art that the concepts discussed and many of the disclosed embodiments are applicable to other types of molecule detection (e.g., inorganic molecules).

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

I claim:

1. A detection device, comprising:
   one or more pole pieces;
   at least one magnetic component configured to generate a magnetic field through the one or more pole pieces;
   a plurality of sensors, each of the plurality of sensors coupled to at least one of the one or more pole pieces; and
   detection circuitry coupled to the plurality of sensors, wherein the detection circuitry is configured to detect a characteristic of each of the plurality of sensors, the characteristic indicating presence or absence of one or more magnetic nanoparticles (MNPs) coupled to at least one of a plurality of molecules to be detected;
   and wherein:
   at least one of the one or more pole pieces is operable to draw the one or more MNPs toward at least one of the plurality of sensors;
   a first subset of the plurality of sensors is arranged in a first row;
   a second subset of the plurality of sensors is arranged in a second row, the second row being substantially parallel to the first row; and
   at least one reagent area is disposed between the first and second rows.

2. The detection device recited in claim 1, wherein the at least one reagent area is configured to hold fluid containing the plurality of molecules to be detected.

3. The detection device recited in claim 2, wherein the at least one reagent area comprises a fluidic channel.

4. The detection device recited in claim 1, wherein:
   one or more surfaces within the at least one reagent area provide one or more sites for binding the plurality of molecules to be detected, the one or more sites being located among the plurality of sensors.

5. The detection device recited in claim 4, wherein the one or more sites comprise a plurality of sites, and further comprising at least one magnetic shield disposed between at least two of the plurality of sites.

6. The detection device recited in claim 1, further comprising:
   a barrier material encapsulating the plurality of sensors and for providing a barrier between the plurality of sensors and the plurality of molecules to be detected.

7. The detection device recited in claim 6, wherein the barrier material comprises an insulator or a metal.

8. The detection device recited in claim 1, wherein the characteristic comprises:
   a voltage, current, resistance, frequency, phase, noise, or temperature; or
   a change in voltage, current, resistance, frequency, phase, noise, or temperature; or
   a change in a statistical property of voltage, current, resistance, frequency, phase, noise, or temperature.

9. The detection device recited in claim 1, wherein the plurality of sensors comprises a temperature sensor, a magnetoresistive (MR) sensor, a magnetic tunnel junction (MTJ), a spin-torque oscillator (STO), or a spin valve.

10. The detection device recited in claim 1, wherein at least one of the one or more pole pieces has a conical, triangular, or pyramidal shape.

11. The detection device recited in claim 1, wherein at least one of the one or more pole pieces is configured to assist in creating a magnetic field gradient for drawing at least a portion of the one or more MNPs toward at least one of the plurality of sensors.

12. The detection device recited in claim 1, wherein the plurality of sensors is disposed in a cross-point array comprising a first top line, a second top line, a first bottom line, and a second bottom line, wherein:
the first top line is coupled to the first bottom line at a first location,
the first top line is coupled to the second bottom line at a second location,
the second top line is coupled to the first bottom line at a third location, and
the second top line is coupled to the second bottom line at a fourth location.

13. The detection device recited in claim 12, wherein:
the first and second top lines are substantially parallel to each other,
the first and second bottom lines are substantially parallel to each other, and
the first and second top lines are substantially perpendicular to the first and second bottom lines.

14. The detection device recited in claim 1, wherein the detection device is a sequencing device, and wherein the plurality of molecules to be detected comprises biologic molecules.

15. The detection device recited in claim 14, wherein the biologic molecules are nucleic acids.

16. The detection device recited in claim 1, wherein the detection circuitry comprises:
one or more selector devices, at least one of the one or more selector devices coupled to a respective one of the plurality of sensors.

17. The detection device recited in claim 16, wherein at least one of the one or more selector devices comprises a transistor.

18. The detection device recited in claim 16, wherein at least one of the one or more selector devices comprises an in-stack selector.

19. An apparatus for molecule detection, the apparatus comprising:
a pole piece;
a solenoid or ferromagnetic component configured to generate a magnetic field through the pole piece;
a sensor disposed between and coupled to the pole piece and the solenoid or ferromagnetic component, wherein the sensor is capable of sensing presence or absence of a magnetic nanoparticle (MNP) label coupled to a molecule to be detected, wherein the presence or absence of the MNP label is reflected by a change in a characteristic of the sensor; and
detection circuitry coupled to the sensor and configured to detect the characteristic of the sensor, wherein the detected characteristic indicates whether the MNP label is present or absent.

20. The apparatus recited in claim 19, further comprising a yoke, wherein the solenoid or ferromagnetic component is disposed between the sensor and the yoke, thereby forming a magnetic circuit.

21. The apparatus recited in claim 20, wherein the solenoid or ferromagnetic component is a ferromagnetic component having a coercivity enabling the ferromagnetic component to be selectively magnetized or selectively demagnetized by an external magnetic field.

22. The apparatus recited in claim 21, wherein a remanence of the ferromagnetic component is selected to enable the ferromagnetic component to detect the MNP label.

23. A method of using the apparatus recited in claim 21, comprising:
applying the external magnetic field to selectively magnetize or to selectively demagnetize the ferromagnetic component.

24. A method of using the apparatus recited in claim 20, comprising:
detecting the presence or absence of the MNP label by detecting a change in a reluctance of the magnetic circuit.

25. The apparatus recited in claim 19, further comprising:
a reagent area configured to hold fluid containing the molecule to be detected.

26. A method of nucleic acid sequencing using a detection device comprising a pole piece, a magnetic component configured to generate a magnetic field through the pole piece, a sensor coupled to the pole piece, a reagent area, and detection circuitry coupled to the sensor, the method comprising:
magnetically labeling a nucleotide precursor with one or more magnetic nanoparticles (MNPs);
adding the magnetically-labeled nucleotide precursor to the reagent area;
after adding the magnetically-labeled nucleotide precursor to the reagent area, detecting a characteristic of the sensor, wherein a change in the characteristic of the sensor indicates presence or absence of at least one of the one or more MNPs; and
based at least in part on the detected characteristic, determining whether the magnetically-labeled nucleotide precursor is present or absent.

27. The method of claim 26, further comprising:
binding a nucleic acid strand to be sequenced to the detection device in the reagent area before adding the magnetically-labeled nucleotide precursor to the reagent area.

28. The method of claim 26, further comprising:
applying a magnetic field to the detection device; and
using the detection circuitry, detecting the characteristic of the sensor while the magnetic field is being applied.

29. The method of claim 28, further comprising:
after detecting the characteristic of the sensor, turning off the magnetic field; and
while the magnetic field is off:
removing at least some of the one or more MNPs, and
washing the at least one reagent area.

30. The method of claim 26, further comprising:
in response to determining that the magnetically-labeled nucleotide precursor is present, recording an identity of the magnetically-labeled nucleotide precursor or an identity of a base complementary to the magnetically-labeled nucleotide precursor.

* * * * *